US009945869B2

(12) United States Patent
Stubenrauch et al.

(10) Patent No.: US 9,945,869 B2
(45) Date of Patent: Apr. 17, 2018

(54) METHOD FOR THE DETECTION OF A BINDING PARTNER OF A MULTISPECIFIC BINDER

(71) Applicant: Hoffmann-La Roche Inc., Little Falls, NJ (US)

(72) Inventors: Kay-Gunnar Stubenrauch, Penzberg (DE); Uwe Wessels, Penzberg (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 123 days.

(21) Appl. No.: 14/449,437

(22) Filed: Aug. 1, 2014

(65) Prior Publication Data
US 2014/0342382 A1 Nov. 20, 2014

Related U.S. Application Data

(63) Continuation of application No. PCT/EP2013/051604, filed on Jan. 29, 2013.

(30) Foreign Application Priority Data

Feb. 1, 2012 (EP) ..................................... 12153457
Aug. 31, 2012 (EP) ..................................... 12182505

(51) Int. Cl.
*G01N 33/53* (2006.01)
*G01N 33/68* (2006.01)
*G01N 33/543* (2006.01)

(52) U.S. Cl.
CPC ... *G01N 33/6854* (2013.01); *G01N 33/54306* (2013.01); *G01N 2333/00* (2013.01)

(58) Field of Classification Search
None
See application file for complete search history.

(56) References Cited

U.S. PATENT DOCUMENTS

| 5,219,730 | A | 6/1993 | Potocnjak et al. |
| 6,753,189 | B1 | 6/2004 | Narahara et al. |
| 2008/0206782 | A1 | 8/2008 | Golden et al. |
| 2013/0231462 | A1* | 9/2013 | Roth ...................... C07K 16/42 530/387.2 |
| 2015/0072359 | A1 | 3/2015 | Stubenrauch et al. |
| 2015/0198608 | A1 | 7/2015 | Stubenrauch et al. |

FOREIGN PATENT DOCUMENTS

| CN | 101268372 A | 9/2008 |
| EP | 0 139 389 A1 | 5/1985 |
| EP | 0 170 302 A1 | 2/1986 |
| EP | 0 580 979 A2 | 2/1994 |
| EP | 0 651 761 A1 | 5/1995 |
| EP | 0 962 771 A1 | 8/1999 |
| EP | 1 917 854 A1 | 5/2008 |
| JP | H09-07096 A | 3/1997 |
| JP | H-11-352129 A | 12/1999 |
| JP | 2001-524674 A | 12/2001 |
| JP | 2011-523853 A | 8/2011 |
| WO | WO-87/02778 A1 | 5/1987 |
| WO | WO-90/05301 A1 | 5/1990 |
| WO | WO-90/11511 A1 | 10/1990 |
| WO | WO-92/14138 A1 | 8/1992 |
| WO | WO-99/27368 A1 | 6/1999 |
| WO | 2006/096697 A2 | 9/2006 |
| WO | WO-2007/009469 A2 | 1/2007 |
| WO | WO-2009/080251 A1 | 7/2009 |
| WO | WO-2009/080252 A1 | 7/2009 |
| WO | WO-2009/080253 A1 | 7/2009 |
| WO | WO-2009/080254 A1 | 7/2009 |
| WO | WO-2009/149189 A2 | 12/2009 |
| WO | WO-2010/112193 A1 | 10/2010 |
| WO | WO-2010/115589 A1 | 10/2010 |
| WO | WO-2010/136172 A1 | 12/2010 |
| WO | WO-2010/145792 A1 | 12/2010 |
| WO | WO-2010/145793 A1 | 12/2010 |

OTHER PUBLICATIONS

Almagro et al. "Humanization of Antibodies," *Frontiers in Bioscience* 13:I6I9-I633, (Jan. 1, 2008).
Butler, "Solid Phases in Immunoassay," Chapter 9 in *Immunochemistry of Solid Phase Immunoassay*, pp. 205-225, (1996).
Butler. "Solid Supports in Enzyme-Linked Immunosorbent Assay and Other Solid-Phase Immunoassays," *Methods* 22(1):4-23 (2000).
Certified Priority Document of Europe Patent Application No. 12153457.2, filed on Feb. 1, 2012, for PCT Application No. PCT/EP2013/051604, filed on Jan. 29, 2013, 41 pages.
Certified Priority Document of Europe Patent Application No. 12182505.3, filed on Aug. 31, 2012, for PCT Application No. PCT/EP2013/051604, filed on Jan. 29, 2013, 52 pages.
Chothia et al. "Canonical Structures for the Hypervariable Regions of Immunoglobulins," *J. Mol. Biol.* I96:90I-9I7, (1987).
Clackson et al. "Making Antibody Fragments Uisng Phage Display Libraries," *Nature* 352:624-628, (Aug. 15, 1991).
Hage. "Immunoassays," *Anal. Chem.* 71(12):294R-304R, (Jun. 15, 1999, e-pub. May 20, 1999).
Kindt et al. "Antigens and Antibodies," Chapter 4 in *Kuby Immunology*, 6th ed., W.H. Freeman and Co., N.Y., p. 91, (14 pages total), (2007).
Lu et al. "Tutorial Review. Oriented Immobilization of Antibodies and its Applications in Immunoassays and Immunosensors," *Analyst* 121:29R-32R, (Mar. 1996).

(Continued)

*Primary Examiner* — Changhwa J Cheu
(74) *Attorney, Agent, or Firm* — Morrison & Foerester LLP

(57) ABSTRACT

Herein is reported a method for the detection of free antigen of a multispecific antibody in a sample, whereby the antigen to be detected can be specifically bound by a first binding site of the multispecific antibody, comprising the step of incubating a sample comprising free antigen and multispecific antibody with an anti-idiotypic antibody, which specifically binds to a second binding specificity of the bispecific antibody, which is different from the first binding specificity, whereby the anti-idiotypic antibody is bound to a solid phase.

8 Claims, 15 Drawing Sheets

(56) References Cited

OTHER PUBLICATIONS

Martin et al. "Peer Reviewed: Nanomaterials in Analytical Chemistry," *Analytical Chemistry-News & Features* 70:322A-327A, (May 1, 1998).
Portolano et al. "Lack of Promiscuity in Autoangigen-Specific H and L Chain Combinations as Revelaed by Human H and L Chain "Roulette"," *J. Immunol.* 150(3):880-887, (Feb. 1, 1993).
Wadhwa et al. "Strategies for Detection, Measurement and Characterization of Unwanted Antibodies Induced by Therapeutic Biologicals," *J. Immunol. Methods* 278:1-17,(2003).
Wilchek et al. "Avidin-Biotin Mediated Immunoassays: Overview," *Methods Enzymol.* 184:467-469, (1990).
International Search Report mailed on Jun. 24, 2013, for PCT Application No. PCT/EP2013/051604, filed on Jan. 1, 2013, 7 pages.
Written Opinion mailed on Jun. 24, 2013, for PCT Application No. PCT/EP2013/051604, filed on Jan. 1, 2013, 12 pages.
Berkova et al., "Development of an Enzyme Immunoassay for the Measurement of Human Tumour Necrosis Factor-x (hTNF-x) Using Bispecific Antibodies to hTNF-x and Horseradish Peroxidase" Biotechnology and Applied Biochemistry 23(2):163-171 (Apr. 1, 1996).
Bruynck et al., "Characterization of a Humanised Bispecific Monoclonal Antibody for Cancer Therapy" British Journal of Cancer 67(3):436-440 (Mar. 1, 1993).
Chen et al., "Rapid Detection of Hepatitis B Virus Surface Antigen by an Agglutination Assay Mediated by a Bispecific Diabody Against Both Human Erythrocytes and Hepatitis B Virus Surface Antigen" Clinical and Vaccine Immunology 14(6):720-725 (Apr. 18, 2007).
Doppalapudi et al., "Chemical Generation of Bispecific Antibodies" PNAS 107(52):22611-22616 (Dec. 28, 2010).
Porter et al., "An Electro-Active System of Immuno-Assay (EASI Assay) Utilizing Self Assembled monolayer Modified Electrodes" Biosensors & Bioelectronics 16(9-12):875-885 (Dec. 1, 2001).
Reinartz et al., "Bispecific Multivalent Antibody Studies by Real-Time Interaction Analysis for the Development of an Antigen-Inhibition Enzyme-Linked Immunosorbent Assay" Analyst 121(6):767-771 (Jun. 1, 1996).
Aslam et al. "The Functional Chemistry of Proteins and Protein Coupling," Chapter 2 in Bioconjugation. Protein Coupling Techniques for the Biomedical Sciences, MacMillan Reference Ltd., Hampshire, England, pp. 50-100, (1998).

* cited by examiner

METHOD FOR THE DETECTION OF A BINDING PARTNER OF A MULTISPECIFIC BINDER

RELATED APPLICATIONS

This application is a continuation of International Application No. PCT/EP2013/051604 having an international filing date of Jan. 29, 2013, the entire contents of which are incorporated herein by reference, and which claims benefit under 35 U.S.C. § 119 to European Patent Application Nos. 12153457.2, filed Feb. 1, 2012, and 12182505.3, filed Aug. 31, 2012.

The current invention is directed to a method for the detection/determination of free, i.e. non-complexed, binding partner of a multispecific binder which can be specifically bound by a multispecific binder in a sample, wherein binding partner bound to the multispecific binder is depleted from the sample prior to the detection of the free binding partner. The depleted multispecific binder can be used for the detection/determination of complexed binding partner.

BACKGROUND OF THE INVENTION

Standard solid-phase immunoassays with antibodies involve the formation of a complex between an antibody adsorbed/immobilized on a solid phase (capture antibody), the antigen, and an antibody to another epitope of the antigen conjugated with an enzyme or detectable label (tracer antibody). In the assay, a sandwich is formed: solid phase/capture antibody/antigen/tracer antibody. In the reaction catalyzed by the sandwich among other things the activity of the antibody-conjugated enzyme is proportional to the antigen concentration in the incubation medium. Anti-idiotypic antibody assays are mentioned, for example, in U.S. Pat. No. 5,219,730; WO 87/002778; EP 0 139 389; and EP 0 170 302. Wadhwa, M., et al. (J. Immunol. Methods 278 (2003) 1-17) report strategies for the detection, measurement and characterization of unwanted antibodies induced by therapeutic biologicals. A method for producing anti idiotypic antibodies is reported in EP 1 917 854.

Chen, Y.-P., et al. (Clin. Vac. Immunol. 14 (2007) 720-725) report the rapid detection of hepatitis B virus surface antigen by an agglutination assay mediated by a bispecific diabody against both human erythrocytes and hepatitis B virus surface antigen. Porter, R., et al report an electro-active system of immuno-assay (EASI assay) utilizing self-assembled monolayer modified electrodes (Biosensors Bioelec. 16 (2001) 9-12). The development of an enzyme immunoassay for the measurement of human tumor necrosis factor-alpha (hTNF-alpha) using bispecific antibodies to hTNF-alpha and horseradish peroxidase is reported by Berkova, N., et al. (Biotechnol. Appl. Biochem. 23 (1996) 163-171). In EP 0 962 771 a detection apparatus and method for the same is reported. Reinhartz, H. W., et al. (Analyst 121 (1996) 767-771) report bispecific multivalent antibody studied by real-time interaction analysis for the development of an antigen-inhibition enzyme-linked immunosorbent assay. The chemical generation of bispecific antibodies is reported by Doppalapudi, V. R., et al. (Proc. Natl. Acad. Sci. 107 (2010) 22611-22616).

SUMMARY OF THE INVENTION

Herein is reported a method for the detection of the presence or for the determination of the amount of a free, i.e. non-complexed, binding partner in a sample, whereby the binding partner can be specifically bound by at least one binding specificity of a multispecific binder, i.e. by a first binding specificity.

It has been found that it is advantageous to deplete the binding partner that is specifically bound by the multispecific binder, i.e. the binding partner-multispecific binder-complex, from the sample prior to the determination of the amount of free binding partner.

According to the methods as reported herein is the depletion of the multispecific binder achieved by incubating the sample either with a binding partner, i.e. with a second binding partner, that can be specifically bound by a different, i.e. second, binding specificity of the multispecific binder which does not bind to the binding partner to be determined, i.e. the first binding partner, or with a monospecific binder that specifically binds to one binding specificity of the multispecific binder, whereby the monospecific binder specifically binds to a binding specificity of the multispecific binder that does not bind to the binding partner to be determined (see FIG. 2).

One aspect as reported herein is an in vitro method for the determination of the presence and/or the amount of an (first) antigen of a bispecific antibody in a sample, whereby the antigen to be detected can be specifically bound by a first binding specificity of the bispecific antibody, and whereby the antigen is complexed to the bispecific antibody (antigen-bispecific antibody-complex), comprising the step of:
  incubating a sample comprising the antigen and the bispecific antibody with an anti-idiotypic antibody, which specifically binds to the second binding specificity of the bispecific antibody, which is different from the first binding specificity, whereby the anti-idiotypic antibody is bound to a solid phase.

In one embodiment the method comprises the steps of:
  incubating a sample comprising the antigen and the bispecific antibody with an anti-idiotypic antibody, which specifically binds to the second binding specificity of the bispecific antibody, which is different from the first binding specificity, whereby the anti-idiotypic antibody is bound to a solid phase, and
  detecting the complex of antigen-bispecific antibody-anti-idiotypic antibody and thereby determining the presence and/or the amount of the antigen of a bispecific antibody.

In one embodiment the method comprises the steps of:
  incubating a sample comprising the antigen and the bispecific antibody with an anti-idiotypic antibody, which specifically binds to the second binding specificity of the bispecific antibody, which is different from the first binding specificity, whereby the anti-idiotypic antibody is bound to a solid phase, and
  incubating the complex formed in the first step with an antibody that specifically binds to the antigen at an epitope different from the epitope bound by the bispecific antibody and thereby determining the presence and/or the amount of the antigen of a bispecific antibody in a sample.

In one embodiment the method is for the determination of the presence and/or the amount of an antigen of a bispecific antibody which is complexed to the bispecific antibody.

In one embodiment the method comprises the following steps:
  providing a sample comprising the antigen and the bispecific antibody, wherein at least 90% of the antigen are complexed by the bispecific antibody,
  incubating a sample comprising the antigen and the bispecific antibody with an anti-idiotypic antibody, which specifically binds to the second binding specificity of the bispecific antibody, which is different from the first binding specificity, whereby the anti-idiotypic antibody is bound to a solid phase, and incubating the complex formed in the first step with an antibody that specifically binds to the antigen at an epitope different from the epitope bound by the bispecific antibody and thereby determining the presence and/or the amount of the antigen of a bispecific antibody in a sample.

In one embodiment the method comprises the following steps:

incubating a sample comprising the antigen and the bispecific antibody with an amount of the bispecific antibody to provide a sample wherein at least 90% of the antigen is complexed by the bispecific antibody, incubating the sample comprising the antigen complexed by the bispecific antibody with an anti-idiotypic antibody, which specifically binds to the second binding specificity of the bispecific antibody, which is different from the first binding specificity, whereby the anti-idiotypic antibody is bound to a solid phase, and incubating the complex formed in the previous step with an antibody that specifically binds to the antigen at an epitope different from the epitope bound by the bispecific antibody and thereby determining the presence and/or the amount of the antigen of a bispecific antibody in a sample.

In one embodiment the amount of the bispecific antibody is about 1 µg/ml to 10 µg/ml, preferably about 1.5 µg/ml.

In one embodiment the amount of the bispecific antibody is 1 mg/ml sample.

In one embodiment at least 95% of the antigen is complexed by the bispecific antibody. In one embodiment at least 98% of the antigen is complexed by the bispecific antibody.

One aspect as reported herein is an in vitro method for the determination of the amount of antibody-bound (first) antigen of a bispecific antibody in a sample, whereby the antigen can be specifically bound by a first binding specificity of the bispecific antibody, comprising the steps of:

incubating a first aliquot of the sample comprising the antigen and the bispecific antibody with an amount of the bispecific antibody to provide a sample wherein at least 90% of the antigen is complexed by the bispecific antibody, incubating the sample comprising the antigen complexed by the bispecific antibody with an anti-idiotypic antibody, which specifically binds to the second binding specificity of the bispecific antibody, which is different from the first binding specificity, whereby the anti-idiotypic antibody is bound to a solid phase, and incubating the complex formed in the previous step with an antibody that specifically binds to the antigen at an epitope different from the epitope bound by the bispecific antibody and thereby determining the presence and/or the amount of the antigen of a bispecific antibody in a sample and thereby determining the total amount of the antigen present in the sample, incubating a second aliquot of the sample comprising the antigen and the bispecific antibody with an anti-idiotypic antibody, which specifically binds to the second binding specificity of the bispecific antibody, which is different from the first binding specificity, whereby the anti-idiotypic antibody is bound to a solid phase, and incubating the formed complex with an antibody that specifically binds to the antigen at an epitope different from the epitope bound by the bispecific antibody and thereby determining the amount of the free antigen of a bispecific antibody present in the sample, and determining the amount of antibody-bound antigen of a bispecific antibody by the difference between the total amount of the antigen present in the sample and the amount of free antigen present in the sample.

In one embodiment the amount of the bispecific antibody is about 1 µg/ml to 10 µg/ml, preferably about 1.5 µg/ml.

In one embodiment the amount of the bispecific antibody is 1 mg/ml sample.

One aspect as reported herein is a method for the in vitro determination of the presence and/or amount of a binding partner (antigen, target, analyte), which can be specifically bound by a first binding specificity of a multispecific binder, wherein the fraction of binding partner bound to the multispecific binder present in a sample is depleted prior to the detection of the binding partner by incubating the sample with a second binding partner, which can be specifically bound by a second binding specificity of the multispecific binder, or a monospecific binder specifically binding to a second binding specificity of the multispecific binder.

In one embodiment the binding partner to be detected is non-complexed binding partner or free binding partner.

Thus, one aspect as reported herein is an in vitro method for the determination of the presence and/or the amount of a (first) binding partner of a multispecific binder, whereby the binding partner can be specifically bound by a first binding specificity of the multispecific binder, comprising the step of:

incubating a sample comprising (first) binding partner and multispecific binder with a second binding partner that can be specifically bound by a second binding specificity of the multispecific binder which is different from the first binding specificity.

In one embodiment the method comprises the steps of:

incubating a sample comprising (first) binding partner and multispecific binder with a monospecific binder that specifically binds to a second binding specificity of the multispecific binder which is different from the first binding specificity, and determining the amount of the (free first) binding partner in the multispecific binder-depleted sample.

In one embodiment the method comprises the step of:

incubating a sample comprising (first) binding partner and multispecific binder with an monospecific binder that specifically binds to a second binding specificity of the multispecific binder which is different from the first binding specificity, depleting the monospecific binder-multispecific binder-complex from the sample prior to the determination of the presence or the amount of free binding partner, and determining the amount of the (free first) binding partner in the multispecific binder-depleted sample.

By the incubation with the second binding partner that can be specifically bound by a second binding specificity of the multispecific binder the multispecific binder is removed/depleted from the sample. Concomitantly also (first) binding partner-multispecific binder-complexes are removed from the sample.

In one embodiment the multispecific binder is selected from an antibody, a fusion polypeptide comprising an antibody or antibody fragment and non-antibody polypeptide, a fusion polypeptide comprising an antibody or antibody fragment and a soluble receptor, or a fusion polypeptide comprising an antibody or antibody fragment and a peptidic binding molecule.

In one embodiment the multispecific binder is an antibody. In one embodiment the antibody is a bispecific antibody, or a trispecific antibody, or a tetraspecific antibody, or a pentaspecific antibody, or a hexaspecific antibody. In one embodiment the antibody is a bispecific antibody.

In one embodiment the monospecific binder is an antiidiotypic antibody.

In one embodiment the binding specificity is a binding site or a pair of an antibody heavy chain variable domain and an antibody light chain variable domain.

In one embodiment the second binding partner or the monospecific binder is bound to a solid phase.

In one embodiment the second binding partner is biotinylated and the solid phase is streptavidin coated. In one embodiment the solid phase is a streptavidin coated paramagnetic bead or a streptavidin coated sepharose bead.

One aspect as reported herein is a method for the immunological determination of the presence and/or amount of a binding partner of a multispecific binder in a sample using an immunoassay, wherein the multispecific binder is depleted from the sample prior to the determination of the binding partner.

In one embodiment of all aspects as reported herein the binding partner is the free binding partner, i.e. binding partner that is not bound or complexed by the multispecific binder.

In one embodiment the second binding partner is a biotinylated second binding partner and is conjugated to a solid phase via streptavidin.

In one embodiment of the methods as reported herein the second binding partner is a mixture comprising at least two second binding partners that differ in the site at which they are conjugated to the solid phase. In one embodiment the site is the amino acid position of the amino acid sequence of the second binding partner.

In one embodiment the first binding partner is a polypeptide.

In one embodiment the second binding partner is a polypeptide.

In one embodiment the conjugation of a polypeptide to its conjugation partner is performed by chemically binding via N-terminal and/or ε-amino groups (lysine), ε-amino groups of different lysins, carboxy-, sulfhydryl-, hydroxyl- and/or phenolic functional groups of the amino acid backbone of the polypeptide and/or sugar alcohol groups of the carbohydrate structure of the polypeptide.

In one embodiment the second binding partner is a mixture comprising the second binding partner conjugated via at least two different amino groups to the solid phase. Such coupling via different amino groups can be performed by acylation of a part of the ε-amino groups with chemical protecting agents, e.g. by citraconylation, in a first step. In a second step conjugation is performed via the remaining amino groups. Subsequently citraconylation is removed and the binding partner is conjugated to the solid phase via remaining free amino groups, i.e. the binding partner obtained is conjugated to the solid phase via amino groups that have not been protected by citraconylation. Suitable chemical protecting agents form bonds at unprotected side chain amines and are less stable than and different from those bonds at the N-terminus. Many such chemical protecting agents are known (see for example EP 0 651 761). In one embodiment the chemical protecting agents include cyclic dicarboxylic acid anhydrides like maleic or citraconylic acid anhydride.

In one embodiment the second binding partner is conjugated to the solid phase by passive adsorption. Passive adsorption is, e. g., described by Butler, J. E., in "Solid Phases in Immunoassay" (1996) 205-225 and Diamandis, E. P., and Christopoulos, T. K. (Editors), in "Immunoassay" (1996) Academic Press (San Diego).

In one embodiment the second binding partner is conjugated (immobilized) via a specific binding pair. Such a binding pair (first component/second component) is in one embodiment selected from streptavidin or avidin/biotin, antibody/antigen (see, for example, Hermanson, G. T., et al., Bioconjugate Techniques, Academic Press (1996)), lectin/polysaccharide, steroid/steroid binding protein, hormone/hormone receptor, enzyme/substrate, IgG/Protein A and/or G, etc. In one embodiment the second binding partner is conjugated to biotin and immobilization is performed via immobilized avidin or streptavidin.

One aspect as reported herein is an in vitro method for the determination of the presence and/or amount of an (first) antigen of a multispecific antibody in a sample, whereby the antigen to be detected can be specifically bound by a first binding specificity of the multispecific antibody, comprising the step of:

incubating a sample comprising the multispecific antibody, multispecific antibody bound (first) antigen and free (first) antigen with a second antigen that can be specifically bound by a second binding specificity of the multispecific antibody, which is different from the first binding specificity.

In one embodiment the method comprises the steps of:

incubating a sample comprising the multispecific antibody, multispecific antibody bound (first) antigen and free (first) antigen with a second antigen that can be specifically bound by a second binding specificity of the multispecific antibody, which is different from the first binding specificity, and determining the amount of the (first) antigen in the multispecific antibody-depleted sample.

In one embodiment the method comprises the step of:

incubating a sample comprising (first) antigen and multispecific antibody with the second antigen that can specifically be bound by the second binding specificity of the multispecific antibody which is different from the first binding specificity, depleting the second antigen-multispecific antibody-complex from the sample prior to the determination of the presence or the amount of free antigen, and determining the amount of the (first) antigen in the multispecific antibody-depleted sample.

By the incubation with the second antigen that can be specifically bound by a second binding specificity of the multispecific antibody the multispecific antibody is removed from the sample. Concomitantly also (first) antigen-multispecific antibody-complexes are removed from the sample.

In one embodiment the sample comprises multispecific antibody, free (first) antigen and multispecific antibody-antigen complexes and the detection is of free (first) antigen of the multispecific antibody.

In one embodiment the second antigen is conjugated to a paramagnetic bead.

In one embodiment the second antigen is conjugated to a solid phase.

In one embodiment the second antigen is biotinylated and the solid phase is streptavidin coated. In one embodiment the solid phase is a streptavidin coated paramagnetic bead or a streptavidin coated sepharose bead.

In one embodiment the binding specificity is a binding site. In one embodiment the binding site is a pair of an antibody heavy chain variable domain and an antibody light chain variable domain.

In one embodiment the method comprises the following steps:
incubating a sample comprising the multispecific antibody, multispecific antibody-bound (first) antigen and free (first) antigen with a second antigen that can be specifically bound by a second binding specificity of the multispecific antibody, which is different from the first binding specificity, to form an second antigen-multispecific antibody complex, and
removing the second antigen-multispecific antibody complex from the sample.

In one embodiment the second antigen-multispecific antibody complex is a mixture of second antigen-multispecific antibody complex and second antigen-multispecific antibody-(first) antigen complex.

In one embodiment the method comprises the following steps:
incubating a sample comprising (first) antigen and multispecific antibody with a second antigen that can be specifically bound by a second binding specificity of the multispecific antibody, which is different from the first binding specificity, to form a second antigen-multispecific antibody complex,
removing the second antigen-multispecific antibody complex from the sample, and
determining the amount of the (first) antigen in the multispecific-antibody depleted sample.

In one embodiment the determining of the amount of the (first) antigen comprises the following steps:
incubating a multispecific antibody-depleted sample with a capture antibody that specifically binds to the (first) antigen to form a capture antibody-(first) antigen complex, and
correlating the formed capture antibody-(first) antigen complex to the amount of the (first) antigen in the sample.

In one embodiment the determining of the amount of the (first) antigen comprises the following steps:
incubating a multispecific antibody-depleted sample with a capture antibody that specifically binds to the (first) antigen to form a capture antibody-(first) antigen complex,
incubating the capture antibody-(first) antigen complex with a tracer antibody, whereby the capture antibody and the tracer antibody bind to non-overlapping epitope on the (first) antigen, and
correlating the formed capture antibody-(first) antigen-tracer antibody complex to the amount of the antigen in the sample.

In one embodiment the determining of the amount of the (first) antigen comprises the following steps:
incubating a multispecific antibody-depleted sample with a capture antibody that specifically binds to the (first) antigen to form a capture antibody-(first) antigen complex,
incubating the capture antibody-(first) antigen complex with a tracer antibody, whereby the capture antibody and the tracer antibody bind to non-overlapping epitope on the (first) antigen,
incubating the capture antibody-(first) antigen-tracer antibody complex with a detection antibody comprising a detectable label, whereby the detection antibody specifically binds to the tracer antibody at an epitope outside the variable domains of the tracer antibody, and
correlating the formed capture antibody-(first) antigen-tracer antibody complex to the amount of the (first) antigen in the sample.

In one embodiment the multispecific antibody is a bispecific antibody that has a first binding specificity that specifically binds to a first antigen or first epitope on an antigen and that has a second binding specificity that specifically binds to a second antigen or to a second epitope on the antigen.

In one embodiment the first antigen and the second antigen are the same antigen and the first binding specificity binds to a first epitope on the antigen and the second binding specificity binds to a second epitope on the antigen whereby the second epitope is a non-overlapping epitope to the first epitope and the binding of the first binding specificity does not interfere with the binding of the second binding specificity.

In one embodiment the method comprises the step of:
depleting the formed complex from the sample prior to the determination of the presence or the amount of the (first) antigen.

One aspect as reported herein is an in vitro method for the determination of the presence and/or the amount of an (first) antigen of a multispecific antibody in a sample, whereby the antigen to be detected can be specifically bound by a first binding specificity of the multispecific antibody, comprising the step of:
incubating a sample comprising the (first) antigen with a complex of bispecific antibody and second antigen or a complex of bispecific antibody and anti-idiotypic antibody, which specifically binds to the second binding specificity of the bispecific antibody, which is different from the first binding specificity.

In one embodiment the second antigen is a labeled second antigen. In one embodiment the second antigen is immobilized via a specific binding pair to a solid phase. In one embodiment the specific binding pair is biotin and streptavidin.

In one embodiment the method comprises as second step:
incubating the complex formed in the first step with an antibody that specifically binds to the first antigen at an epitope different from the epitope bound by the bispecific antibody.

One aspect as reported herein is an in vitro method for the determination of the presence and/or the amount of an (first) antigen of a bispecific antibody in a sample, whereby the antigen to be detected can be specifically bound by a first binding specificity of the bispecific antibody, comprising the step of:
incubating a sample comprising the (first) antigen with bispecific antibody and second antigen or bispecific antibody and anti-idiotypic antibody, which specifically binds to the second binding specificity of the bispecific antibody, which is different from the first binding specificity, whereby the second antigen or the anti-idiotypic antibody is bound to a solid phase.

In one embodiment the method comprises as second step:
incubating the complex formed in the first step with an antibody that specifically binds to the first antigen at an epitope different from the epitope bound by the bispecific antibody and thereby determining the amount of a (first) antigen of a bispecific antibody in a sample.

One aspect as reported herein is an in vitro method for the determination of the presence and/or the amount of an (first) antigen of a bispecific antibody in a sample complexed to the bispecific antibody (first antigen-bispecific antibody-complex), whereby the antigen to be detected can be specifically bound by a first binding specificity of the bispecific antibody, comprising the step of:

incubating a sample comprising the (first) antigen and the bispecific antibody with an anti-idiotypic antibody, which specifically binds to the second binding specificity of the bispecific antibody, which is different from the first binding specificity, whereby the anti-idiotypic antibody is bound to a solid phase.

In one embodiment the method comprises as second step:

incubating the complex formed in the first step with an antibody that specifically binds to the first antigen at an epitope different from the epitope bound by the bispecific antibody and thereby determining the amount of a (first) antigen of a bispecific antibody complexed to the bispecific antibody (first antigen-bispecific antibody-complex) in a sample.

In one embodiment the method comprises the step of:

depleting the formed complex from the sample prior to the determination of the presence or the amount of the (first) antigen.

DETAILED DESCRIPTION OF THE INVENTION

Herein is reported an in vitro method for the pre-treatment of a sample to detect "free and/or total binding partner" of multispecific binders, such as bispecific antibodies/drugs, in pre-clinical and clinical samples.

It has been found that it is advantageous to be depleted the multispecific binder from the sample prior to the detection of the free binding partner.

It has been found that it is advantageous to incubate the sample with samples multispecific binder in order to convert about the total binding partner in the sample into a defined complex.

It has been found that the capture of the multispecific binder using an anti-idiotypic antibody is advantageous.

Herein is reported the use of a second binding partner that can be specifically bound by a second binding specificity of a therapeutic multispecific antibody in the determination of the level of (free first) antigen that can be but is not bound by a first binding specificity of the multispecific therapeutic antibody. The second antigen is used for the depletion of the multispecific antibody and multispecific antibody-antigen to be detected-complexes from a sample.

Thus, herein is reported an in vitro method for the determination of free (first) binding partner (antigen, target, analyte) of a multispecific binder that can be specifically bound by a first binding specificity of the multispecific binder, wherein the multispecific binder is depleted from the sample prior to the determination of the free binding partner by incubating the sample with a second binding partner that can be specifically bound by a second binding specificity of the multispecific binder, which is different from the first binding specificity, and therewith depletes the multispecific binder and multispecific binder-(first) binding partner-complexes from the sample.

In the following the method as reported herein is exemplified with a multispecific antibody which specifically binds to a multitude of antigens or epitopes on the same antigen as embodiment of a multispecific binder and with an (first) antigen which can be specifically bound by a first binding specificity of a multispecific antibody as embodiment of (first) binding partner.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity.

In certain embodiments, the antibody is a multispecific antibody, e.g. a bispecific antibody. Multispecific antibodies are monoclonal antibodies that have binding specificities for at least two different sites. In certain embodiments, one of the binding specificities is for a first antigen and the other is for a different second antigen. In certain embodiments, bispecific antibodies may bind to two different epitopes of the same antigen. Bispecific antibodies can be prepared as full length antibodies or antibody fragments. In one embodiment the antibody is a bispecific antibody which specifically binds to a first and a second antigen. In one embodiment the bispecific antibody has i) a first binding specificity that specifically binds to a first antigen or a first epitope on an antigen, and ii) a second binding specificity that specifically binds to a second antigen or a second epitope on the same antigen. In one embodiment the second epitope on the same antigen is a non-overlapping epitope.

Multispecific antibodies are described in WO 2009/080251, WO 2009/080252, WO 2009/080253, WO 2009/080254, WO 2010/112193, WO 2010/115589, WO 2010/136172, WO 2010/145792, or WO 2010/145793.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g. IgG$_1$, IgG$_2$, IgG$_3$, IgG$_4$, IgA$_1$, and IgA$_2$. The heavy chain constant domains that correspond to the different classes of immunoglobulins are called $\alpha$, $\delta$, $\epsilon$, $\gamma$, and $\mu$, respectively.

The term "free antigen" denotes the antigen that can be specifically bound by a binding specificity of an antibody but which is currently not bound to this binding specificity. In one embodiment the free antigen is a not-antibody bound antigen or a non-antibody complexed antigen.

The term "Fc-region" herein is used to define a C-terminal region of an immunoglobulin heavy chain that contains at least a portion of the constant region. The term includes native sequence Fc-regions and variant Fc-regions. In one embodiment, a human IgG heavy chain Fc-region extends from Cys226, or from Pro230, to the carboxyl-terminus of the heavy chain. However, the C-terminal lysine (Lys447) of the Fc-region may or may not be present. Unless otherwise specified herein, numbering of amino acid residues in the Fc-region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3 (L3)-FR4.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g. a non-human antibody, refers to an antibody that has undergone humanization.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917). Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3 (Kabat, E. A. et al., Sequences of Proteins of Immunological Interest, 5th ed. Public Health Service, National Institutes of Health, Bethesda, Md. (1991), NIH Publication 91-3242). With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3 (Almagro, J. C. and Fransson, J., Front. Biosci. 13 (2008) 1619-1633). Unless otherwise indicated, HVR residues and other residues in the variable domain (e.g. FR residues) are numbered herein according to Kabat et al., supra.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "polypeptide" is a polymer consisting of amino acids joined by peptide bonds, whether produced naturally or synthetically. Polypeptides of less than about 20 amino acid residues may be referred to as "peptides", whereas molecules consisting of two or more polypeptides or comprising one polypeptide of more than 100 amino acid residues may be referred to as "proteins". A polypeptide may also comprise non-amino acid components, such as carbohydrate groups, metal ions, or carboxylic acid esters. The non-amino acid components may be added by the cell, in which the polypeptide is expressed, and may vary with the type of cell. Polypeptides are defined herein in terms of their amino acid backbone structure or the nucleic acid encoding the same. Additions such as carbohydrate groups are generally not specified, but may be present nonetheless.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs) (see, e.g., Kindt, T. J. et al. Kuby Immunology, 6th ed., W.H. Freeman and Co., N.Y. (2007), page 91). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (see, e.g., Portolano, S. et al., J. Immunol. 150 (1993) 880-887; Clackson, T. et al., Nature 352 (1991) 624-628).

The term "anti-idiotypic antibody" denotes an antibody, which specifically binds to a binding specificity such as a binding site of a parent antibody, i.e. which is directed e.g. against an antigen binding site of a parent antibody. In one embodiment the anti-idiotypic antibody specifically binds to one or more of the CDRs of the parent antibody. In one embodiment the parent antibody is a therapeutic antibody. In one embodiment the parent antibody is a multispecific antibody. In one embodiment the parent antibody is a bispecific antibody.

Two epitopes are overlapping if a signal reduction of 50% or more, in one embodiment of 75% or more, is detected by a surface plasmon resonance (SPR) assay using the immobilized antibody and soluble antigen, or vice versa, with the epitope in question at a concentration of 20-50 nM and the antibody for which the epitope overlap has to be detected at a concentration of 100 nM. Alternatively a method can be used in which epitope overlap of two antibodies binding to the same antigen is determined with the help of a competitive test system. For this purpose, for example with the help of a cell-based enzyme immunoassay (ELISA) employing cells expressing recombinant antigen epitopes, it is tested if the antibody for which the epitope overlap has to be detected competes with the other antibody for the binding to the immobilized antigen. For this purpose, the immobilized antigen is incubated with the antibody in labeled form and an excess of the antibody for which the epitope overlap has to be determined. By detection of the bound labeling there can easily be ascertained the epitope overlap. If a signal reduction of more than 70%, in one embodiment of more than 80%, at the same concentration, or a displacement of more than 80%, in one embodiment of more than 90%, at higher concentrations, in one case with a $10^5$-fold excess of the antibody for which epitope overlap has to be determined, referred to the known antibody is determined then epitope identity or overlap is present and both antibodies bind to the same or an overlapping epitope on the same antigen.

The principles of different immunoassays are described, for example, by Hage, D. S. (Anal. Chem. 71 (1999) 294R-304R). Lu, B., et al. (Analyst 121 (1996) 29R-32R) report the orientated immobilization of antibodies for the use in immunoassays. Avidin-biotin-mediated immunoassays are reported, for example, by Wilchek, M., and Bayer, E. A., in Methods Enzymol. 184 (1990) 467-469.

Polypeptides and monoclonal antibodies and their constant domains contain a number of reactive amino acid side chains for coupling to a binding partner, such as a surface, a protein, a polymer (e.g. PEG, cellulose or polystyrol), an enzyme, or a member of a binding pair. Chemical reactive groups of amino acids are, for example, amino groups (lysins, alpha-amino groups), thiol groups (cystins, cysteines, and methionins), carboxylic acid groups (aspartic acids, glutamic acids), and sugar-alcoholic groups. Such methods are e.g. described by Aslam M., and Dent, A., in "Bioconjugation", MacMillan Ref. Ltd. 1999, pp. 50-100.

One of the most common reactive groups of polypeptides and antibodies is the aliphatic ε-amine of the amino acid lysine. In general, nearly all polypeptides and antibodies contain abundant lysine. Lysine amines are reasonably good nucleophiles above pH 8.0 ($pK_a$=9.18) and therefore react easily and cleanly with a variety of reagents to form stable bonds. Amine-reactive reagents react primarily with lysins and the α-amino groups of proteins. Reactive esters, particularly N-hydroxy-succinimide (NHS) esters, are among the most commonly employed reagents for modification of amine groups. The optimum pH for reaction in an aqueous environment is pH 8.0 to 9.0. Isothiocyanates are amine-modification reagents and form thiourea bonds with proteins. They react with protein amines in aqueous solution (optimally at pH 9.0 to 9.5). Aldehydes react under mild aqueous conditions with aliphatic and aromatic amines, hydrazines, and hydrazides to form an imine intermediate (Schiffs base). A Schiffs base can be selectively reduced with mild or strong reducing agents (such as sodium borohydride or sodium cyanoborohydride) to derive a stable alkyl amine bond. Other reagents that have been used to modify amines are acid anhydrides. For example, diethylenetriaminepentaacetic anhydride (DTPA) is a bifunctional chelating agent that contains two amine-reactive anhydride groups. It can react with N-terminal and ε-amine groups of amino acids to form amide linkages. The anhydride rings open to create multivalent, metal-chelating arms able to bind tightly to metals in a coordination complex.

Another common reactive group in polypeptides and antibodies is the thiol residue from the sulfur-containing amino acid cystine and its reduction product cystine (or half cystine). Cysteine contains a free thiol group, which is more nucleophilic than amines and is generally the most reactive functional group in a protein. Thiols are generally reactive at neutral pH, and therefore can be coupled to other molecules selectively in the presence of amines. Since free sulfhydryl groups are relatively reactive, proteins with these groups often exist with them in their oxidized form as disulfide groups or disulfide bonds. In such proteins, reduction of the disulfide bonds with a reagent such as dithiothreitol (DTT) is required to generate the reactive free thiol. Thiol-reactive reagents are those that will couple to thiol groups on polypeptides, forming thioether-coupled products. These reagents react rapidly at slight acidic to neutral pH and therefore can be reacted selectively in the presence of amine groups. The literature reports the use of several thiolating crosslinking reagents such as Traut's reagent (2-iminothiolane), succinimidyl (acetylthio) acetate (SATA), and sulfo-succinimidyl 6-[3-(2-pyridyldithio)propionamido]hexanoate (Sulfo-LC-SPDP) to provide efficient ways of introducing multiple sulfhydryl groups via reactive amino groups. Haloacetyl derivatives, e.g. iodoacetamides, form thioether bonds and are also reagents for thiol modification. Further useful reagents are maleimides. The reaction of maleimides with thiol-reactive reagents is essentially the same as with iodoacetamides. Maleimides react rapidly at slight acidic to neutral pH.

Another common reactive group in polypeptides and antibodies are carboxylic acids. Polypeptides and antibodies contain carboxylic acid groups at the C-terminal position and within the side chains of aspartic acid and glutamic acid. The relatively low reactivity of carboxylic acids in water usually makes it difficult to use these groups to selectively modify polypeptides and antibodies. When this is done, the carboxylic acid group is usually converted to a reactive ester by the use of a water-soluble carbodiimide and reacted with a nucleophilic reagent such as an amine, hydrazide, or hydrazine. The amine-containing reagent should be weakly basic in order to react selectively with the activated carboxylic acid in the presence of the more highly basic ε-amines of lysine to form a stable amide bond. Protein crosslinking can occur when the pH is raised above 8.0.

Sodium periodate can be used to oxidize the alcohol part of a sugar within a carbohydrate moiety attached to an antibody to an aldehyde. Each aldehyde group can be reacted with an amine, hydrazide, or hydrazine as described for carboxylic acids. Since the carbohydrate moiety is predominantly found on the crystallizable fragment (Fc) region of an antibody, conjugation can be achieved through site-directed modification of the carbohydrate away from the antigen-binding site. A Schiffs base intermediate is formed, which can be reduced to an alkyl amine through the reduction of the intermediate with sodium cyanoborohydride (mild and selective) or sodium borohydride (strong) water-soluble reducing agents.

The term "sample" includes, but is not limited to, any quantity of a substance from a living thing or formerly living thing. Such living things include, but are not limited to, humans, mice, monkeys, rats, rabbits, and other animals. In one embodiment the sample is obtained from a monkey, especially a cynomolgus monkey, or a rabbit, or a mouse or rat. Such substances include, but are not limited to, in one embodiment whole blood, serum, or plasma from an individual, which are the most widely used sources of sample in clinical routine.

The term "solid phase" denotes a non-fluid substance, and includes particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; and cuvettes, tubes or other spectrometer sample containers. A solid phase component is distinguished from inert solid surfaces in that a "solid phase" contains at least one moiety on its surface, which is intended to interact with a substance in a sample. A solid phase may be a stationary component, such as a tube, strip, cuvette or microtiter plate, or may be non-stationary components, such as beads and microparticles. A variety of microparticles that allow either non-covalent or covalent attachment of proteins and other substances may be used. Such particles include polymer particles such as polystyrene and poly(methylmethacrylate); gold particles such as gold nanoparticles and gold colloids; and ceramic particles such as silica, glass, and metal oxide particles. See for example Martin, C. R., et al., Analytical Chemistry-News & Features, 70 (1998) 322A-327A, or Butler, J. E., Methods 22 (2000) 4-23.

From chromogens (fluorescent or luminescent groups and dyes), enzymes, NMR-active groups, metal particles, or haptens, such as digoxygenin, the detectable label is selected in one embodiment. The detectable label can also be a photoactivatable crosslinking group, e.g. an azido or an azirine group. Metal chelates which can be detected by electrochemiluminescense are also in one embodiment signal-emitting groups, with particular preference being given to ruthenium chelates, e.g. a ruthenium (bispyridyl)$_3^{2+}$ chelate. Suitable ruthenium labeling groups are described, for example, in EP 0 580 979, WO 90/05301, WO 90/11511, and WO 92/14138.

Herein is reported a method for the determination of the presence and/or the amount of (free first) antigen of a multispecific antibody in a sample comprising a solid phase immobilized second antigen that can be specifically bound by one binding specificity of the multispecific antibody that is not the binding specificity of the multispecific antibody that specifically binds to the (free first) antigen to be determined for the depletion of the multispecific antibody, either in complexed form or in non-complexed form, from the sample prior to the determination of the amount of the (free first) antigen.

In one embodiment the method comprises the depletion the second antigen-multispecific antibody-complex from the sample prior to the determination of the presence or the amount of free (first) antigen.

In one embodiment the determination of the presence and/or the amount of the (free first) antigen in the multispecific antibody-depleted sample is by an antigen bridging immunoassay. In one embodiment the immunoassay comprises a capture antibody and a tracer antibody, wherein the capture is conjugated to a solid phase, and the tracer antibody is conjugated to a detectable label.

One aspect as reported herein is an in vitro method for the determination of the presence and/or the amount of an (free first) antigen of a multispecific antibody in a sample, whereby the antigen to be detected can be specifically bound by a first binding specificity of the multispecific antibody, comprising the step of:
incubating a sample comprising the (first) antigen and the multispecific antibody with a second antigen that can be specifically bound by a second binding specificity of the multispecific antibody, which is different from the first binding specificity, and thereby removing the multispecific antibody from the sample.

A person skilled in the art knows that a sample that comprises an antigen and an antibody that can specifically bind the antigen comprises a mixture of free antigen, antibody-bound antigen and free antibody due to equilibrium thermodynamics.

In one embodiment the method comprises the following steps:
incubating a sample comprising the (first) antigen and the multispecific antibody with a second antigen that can be specifically bound by a second binding specificity of the multispecific antibody, which is different from the first binding specificity, to form a second antigen-multispecific antibody complex, and
removing the second antigen-multispecific antibody complex from the sample.

In one embodiment the method comprises the following steps:
incubating a sample comprising the (first) antigen and the multispecific antibody with a second antigen that can be specifically bound by a second binding specificity of the multispecific antibody, which is different from the first binding specificity, to form a second antibody-multispecific antibody complex,
removing the second antigen-multispecific antibody complex from the sample, and
determining the amount of the (first) antigen in the multispecific-antibody depleted sample.

In one embodiment the method comprises the step of:
depleting the second antigen-multispecific antibody-complex from the sample prior to the determination of the presence or the amount of free (first) antigen.

In one embodiment the method comprises the step of:
incubating a sample comprising the (first) antigen and multispecific antibody with a second antigen that can be specifically bound by a second binding specificity of the multispecific antibody which is different from the first binding specificity,
depleting the second antigen-multispecific antibody-complex from the sample prior to the determination of the presence or the amount of free (first) antigen, and
determining the amount of the (first) antigen in the multispecific antibody-depleted sample.

In one embodiment the determining the presence and/or the amount of the (first) antigen is by an antigen bridging immunoassay.

In one embodiment the determining of the presence and/or the amount of the (first) antigen is the determining of the amount of the free (first) antigen.

In one embodiment the determining of the presence and/or the amount of the (first) antigen comprises the following steps:
incubating a multispecific antibody-depleted sample with a capture antibody that specifically binds to the (first) antigen to form a capture antibody-antigen complex, and
correlating the amount of formed capture antibody-(first) antigen complex to the amount of the antigen in the sample.

In one embodiment the determining of the presence and/or the amount of the (first) antigen comprises the following steps:
incubating a multispecific antibody-depleted sample with a capture antibody that specifically binds to the (first) antigen to form a capture antibody-(first) antigen complex,
incubating the capture antibody-(first) antigen complex with a tracer antibody, whereby the capture antibody and the tracer antibody bind to non-overlapping epitope on the (first) antigen, and
correlating the formed capture antibody-(first) antigen-tracer antibody complex to the amount of the (first) antigen in the sample.

In one embodiment the tracer antibody comprises a detectable label.

In one embodiment the determining of the presence and/or the amount of the (first) antigen comprises the following steps:
- incubating a multispecific antibody-depleted sample with a capture antibody that specifically binds to the (first) antigen to form a capture antibody-(first) antigen complex,
- incubating the capture antibody-(first) antigen complex with a tracer antibody, whereby the capture antibody and the tracer antibody bind to non-overlapping epitope on the (first) antigen,
- incubating the capture antibody-(first) antigen-tracer antibody complex with a detection antibody comprising a detectable label, whereby the detection antibody specifically binds to the tracer antibody at an epitope outside the variable domains of the tracer antibody, and
- correlating the formed capture antibody-(first) antigen-tracer antibody complex to the amount of the (first) antigen in the sample.

In one embodiment the capture antibody and the tracer antibody bind to non-overlapping epitopes on the (first) antigen.

In one embodiment of the methods as reported herein the (first) antigen is free (first) antigen.

In one embodiment the second antigen and/or the capture antibody are conjugated to a solid phase.

The second antigen and/or the capture antibody useful in a method as reported herein can be conjugated to a solid phase. The conjugation is in one embodiment performed by chemical binding via N-terminal and/or ε-amino groups (lysine), ε-amino groups of different lysins, carboxy-, sulfhydryl-, hydroxyl- and/or phenolic functional groups of the amino acid backbone of the antigen or antibody and/or sugar alcohol groups of the carbohydrate structure of the antigen and/or antibody. The second antigen and/or the capture antibody is in one embodiment a mixture of at least two second antigens and/or antibodies conjugated to a solid phase, wherein the at least two second antigens and/or antibodies conjugated to a solid phase differ in the site at which they are conjugated to the solid phase. For example, the mixture of at least two second antigens and/or two antibodies conjugated to a solid phase may comprise a conjugation via an amino acid of the amino acid backbone to the solid phase and a conjugation via a sugar alcohol group of a carbohydrate structure to the solid phase. Also, for example, the mixture of at least two second antigens and/or two antibodies conjugated to a solid phase may comprise second antigens and/or antibodies conjugated to the solid phase via different amino acid residues of their amino acid backbone. The expression "different amino acid residue" denotes either two different kinds of amino acids, such as e.g. lysine and aspartic acid, or tyrosine and glutamic acid, or two amino acid residues of the amino acid backbone differing in their position in the amino acid sequence of the second antigen and/or antibody. In the latter case the amino acid can be of the same kind or of different kind. The expression "differ in the antibody site" denotes a difference either in the kind of site, e.g. amino acid or sugar alcohol group, or in the number of the amino acid of the amino acid backbone, e.g. at which the second antigen and/or antibody is conjugated to the solid phase. The same applies vice versa to the tracer antibody useful in a method as reported herein.

In one embodiment of the method the immunoassay comprises a capture antibody, a tracer antibody and a detection antibody, wherein the capture antibody is a biotinylated antibody against the antigen conjugated to a solid phase via streptavidin, the tracer antibody is an antibody against the antigen conjugated to digoxygenin, and the detection antibody is an antibody against digoxygenin conjugated to horseradish peroxidase.

The general method for depletion of complexes consisting of bispecific antibodies which specifically bind to antigen X and antigen Y and from samples comprising antigen X and/or antigen Y for the determination of antigen X or antigen Y, respectively, comprises the following steps:
  assembly of complexes between bispecific antibody which specifically binds to antigen X and antigen Y (anti-X/Y antibody):
    A constant concentration of antigen X is incubated with increasing amount of the bispecific monoclonal antibody, which specifically binds to antigen X with a first binding specificity and which specifically binds to antigen Y with a second binding specificity (anti-X/Y antibody), at room temperature for 1 hour. Afterwards, this sample is used as positive control in the depletion step.
  depletion step:
    For depletion of antigen X bound to an anti-X/Y antibody biotinylated antigen Y-BI) is bound to magnetic streptavidin coated beads (SA-beads) at about 10 μg/ml. For each sample, 600 μl SA-beads are washed and separated from supernatant with a magnetic separator. 600 μl of a biotinylated antigen Y containing solution is mixed with the SA-beads and incubated for about one hour at room temperature. The excess of unbound antigen is removed by 3-times washing of the beads with a magnetic separator. Afterwards, the antigen Y coated beads are incubated with about 250 μl of a sample containing complexes of anti-X/Y antibody and antigen X. The mixture is incubated at room temperature with shaking for about one hour. After incubation, the beads are separated from the sample with a magnetic separator. The supernatant is taken for analysis of "free" antigen X in ELISA (see e.g. Example 2). The remaining beads were transferred into ELECSYS container and bead-bound antigen X (bispecific antibody-bound antigen X) is analyzed with ELECSYS 2010 analyzer according standard operational procedures of the user guide.
    For depletion of antigen Y bound to an anti-X/Y antibody biotinylated antigen X (X-BI) is bound to magnetic streptavidin coated beads (SA-beads) at about 10 μg/ml. For each sample, 600 μl SA-beads are washed and separated from supernatant with a magnetic separator. 600 μl of a biotinylated antigen X containing solution is mixed with the SA-beads and incubated for about one hour at room temperature. The excess of unbound antigen X is removed by 3-times washing of the beads with a magnetic separator. Afterwards, the antigen X beads are incubated with about 250 μl of a sample containing complexes of anti-X/Y antibody and antigen Y. The mixture is incubated at room temperature with shaking for about one hour. After incubation, the beads are separated from the sample with a magnetic separator. The supernatant is taken for analysis of "free" antigen Y in ELISA (see e.g. Example 2). The remaining beads were transferred into ELECSYS container and bead-bound antigen Y (bispecific antibody-bound antigen Y) is analyzed with ELECSYS 2010 analyzer according standard operational procedures of the user guide.

For the determination of the pharmacokinetic properties of a multispecific antibody in vivo the distribution or amount of free first antigen, free second antigen, free multispecific antibody, as well as multispecific antibody-first and/or second antigen-complex can be determined.

One aspect as reported herein is an in vitro method suitable for the determination of the presence and/or the amount of free (first) antigen of a bispecific antibody, whereby the (first) antigen can be specifically bound by a first binding specificity of the bispecific antibody, comprising the step of:

incubating a sample comprising (first) antigen and bispecific antibody with an anti-idiotypic antibody that specifically binds to a second binding specificity of the bispecific antibody, which is different from the first binding specificity.

In one embodiment the method comprises the steps of:
incubating a sample comprising (first) antigen and bispecific antibody with an anti-idiotypic antibody that specifically binds to a second binding specificity of the bispecific antibody which is different from the first binding specificity,
removing the anti-idiotypic antibody-bispecific antibody complex from the sample, and
determining the amount of the antigen in the bispecific antibody-depleted sample.

The anti-idiotypic antibody can be bound to a solid phase.

The detection of the bispecific antibody can be performed as immunological determination using a bridging assay comprising a capture molecule, a tracer molecule, and a detection molecule.

The capture molecule can be bound to a solid phase. The capture molecule can be in general any of a binding partner of the bispecific antibody (e.g. one of the antigens), a general complexing agent of the bispecific antibody (e.g. an Fc-receptor or an anti-Fc-region antibody in case of a full length antibody), or an anti-idiotypic antibody that specifically binds to one binding specificity of the bispecific antibody.

The tracer molecule can be any of a binding partner of the multispecific binder (e.g. one of the antigens of the bispecific antibody, but if one antigen is used as capture molecule a different antigen has to be used as tracer molecule), a general complexing agent of the bispecific antibody (e.g. an Fc-receptor in case of a full length antibody with the proviso that this molecule is not already used as capture molecule, or an anti-Fc-region antibody in case of a full length antibody with the proviso that this antibody binds to a different epitope if the same kind of antibody is also used as capture molecule), or a first partner of a binding pair if the bispecific antibody is derivatized with the second partner of a binding pair (with the proviso that a different binding pair is used as that used to immobilized the capture molecule), or an anti-idiotypic antibody that specifically binds to a binding specificity of the bispecific antibody (with the proviso that this binds to a different binding specificity than an anti-idiotypic antibody if used as capture molecule).

One aspect as reported herein is an in vitro method for the determination of the presence and/or the amount of an (first) antigen of a bispecific antibody in a sample complexed to the bispecific antibody (first antigen-bispecific antibody-complex), whereby the antigen to be detected can be specifically bound by a first binding specificity of the bispecific antibody, comprising the step of:

incubating a sample comprising the (first) antigen and the bispecific antibody with an anti-idiotypic antibody, which specifically binds to the second binding specificity of the bispecific antibody, which is different from the first binding specificity, whereby the anti-idiotypic antibody is bound to a solid phase.

In one embodiment an anti-idiotypic antibody-bispecific antibody-(first) antigen-complex is formed in the first step of the method.

In one embodiment the method comprises as second step:
incubating the complex formed in the first step with an antibody that specifically binds to the (first) antigen at an epitope different from the epitope bound by the bispecific antibody and thereby determining the presence and/or the amount of a (first) antigen of a bispecific antibody which is complexed to the bispecific antibody ((first) antigen-bispecific antibody-complex) in a sample.

The determination of total, antibody-bound and free antigen is valuable for monitoring of therapies with therapeutic antibodies. For example, in case of a bispecific antibody specifically binding to ANG2 and VEGF the mechanism of action is blockade of both antigens for binding on their corresponding receptors. In absence of free ligand, the signal pathway is blocked. Thus, a possibility to determine the fraction of free antigen and antibody-bound antigen has influence on therapy, in particular for dose finding and dosing frequency. Total antigen represents the sum of free and (antibody-)bound antigen, During treatment of patients, the antigen and the therapeutic antibody in parallel are present in the patient and complexes thereof are formed. Thus, equilibrium between antibody-bound and free antigen exists in vivo. The location of the equilibrium can be influenced in vitro, e.g. by dilution of the sample or by the selected antibodies for detection or capture. In particular for free antigen, there can be a potential discrepancy between "in vivo" present and "in vitro" determined amount. In addition to the pre-treatment methods, this can be further overcome, by analytical determination of antibody-bound and total antigen, and subsequent determination of free antigen based thereon. Often assay formats for the determination of antibody-bound and total antigen are set up differently, for example the type of assay might be different, antibodies used for capture and detection might be different, sequence and time of incubations steps might be different between the assay used for the determination of antibody-bound antigen and the assay used for the determination of total antigen.

In contrast, in Example 9 and FIG. 13 an assay is described, which can be used for both determination of total antigen and antibody-bound antigen. This unique feature is enabled by the bispecificity of (the therapeutic) antibody and makes use of an anti-idiotypic antibody to the second binding specificity.

Bound target is determined directly in the in vivo sample, e.g. plasma sample.

Simply, by in vitro addition of an excess of bispecific antibody, free antigen present in the sample is converted to antibody-bound antigen. Thus, by carrying out exactly the same assay as for the bound target above for a second time, total antigen is determined. The difference between assay results with and without in vitro addition of bispecific antibody reflect the amount of converted target, i.e. originally present free target.

The following examples and figures are provided to aid the understanding of the present invention, the true scope of which is set forth in the appended claims. It is understood that modifications can be made in the procedures set forth without departing from the spirit of the invention.

EXAMPLE 1

Depletion of Drug-Bound Target (Antibody-Bound Antigen) in Cases of Bispecific Drug Molecules
A) Assembly of Complexes of Bispecific Anti-c-MET/HER3 Antibody and c-MET.

A constant concentration of c-MET was incubated with increasing amount of bispecific antibody which specifically binds to c-MET with a first binding specificity and which specifically binds to HER3 with a second binding specificity (bispecific anti-c-MET/HER3 antibody) at room temperature for 1 hour. Afterwards, these samples were used as positive controls in depletion step.
B) Depletion Step For depletion of c-MET bound to a bispecific anti-c-MET/HER3 antibody biotinylated HER3 (HER3-BI) was bound to magnetic streptavidin coated beads (SA beads) at 10 µg/ml. For each sample, 600 µl SA-beads were washed and separated from supernatant with a magnetic separator. About 600 μl of a HER3-BI containing solution was mixed with the SA-beads and incubated for 1 h at room temperature. The excess of unbound HER3-BI was removed by 3-times washing of the beads with a magnetic separator. Afterwards, antigen coated beads were incubated with 250 μl of samples containing complexes of bispecific anti-c-MET/HER3 antibody and c-MET. Samples were incubated at room temperature with shaking for 1 hour. After incubation, beads were separated from the sample with a magnetic separator. Supernatant was taken for analysis of "free" c-MET in ELISA (see Example 2).

EXAMPLE 2

ELISA for Detection of c-MET

Figure 1:
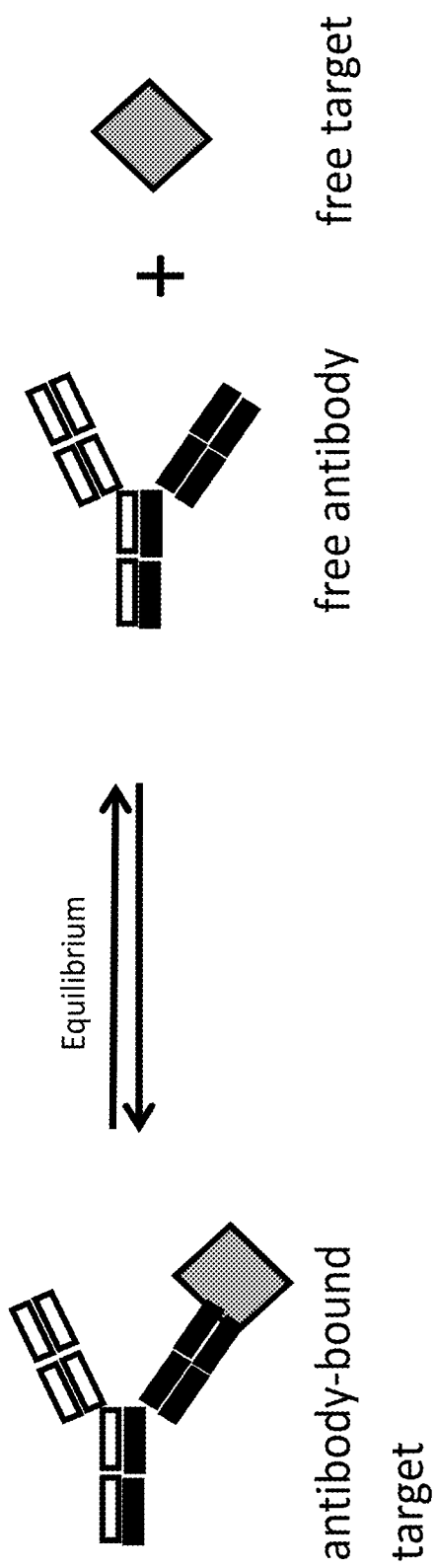
FIG. 1 Equilibrium between drug-bound target (antigen bound to bispecific antibody) and free target (free antigen).
Figure 2:
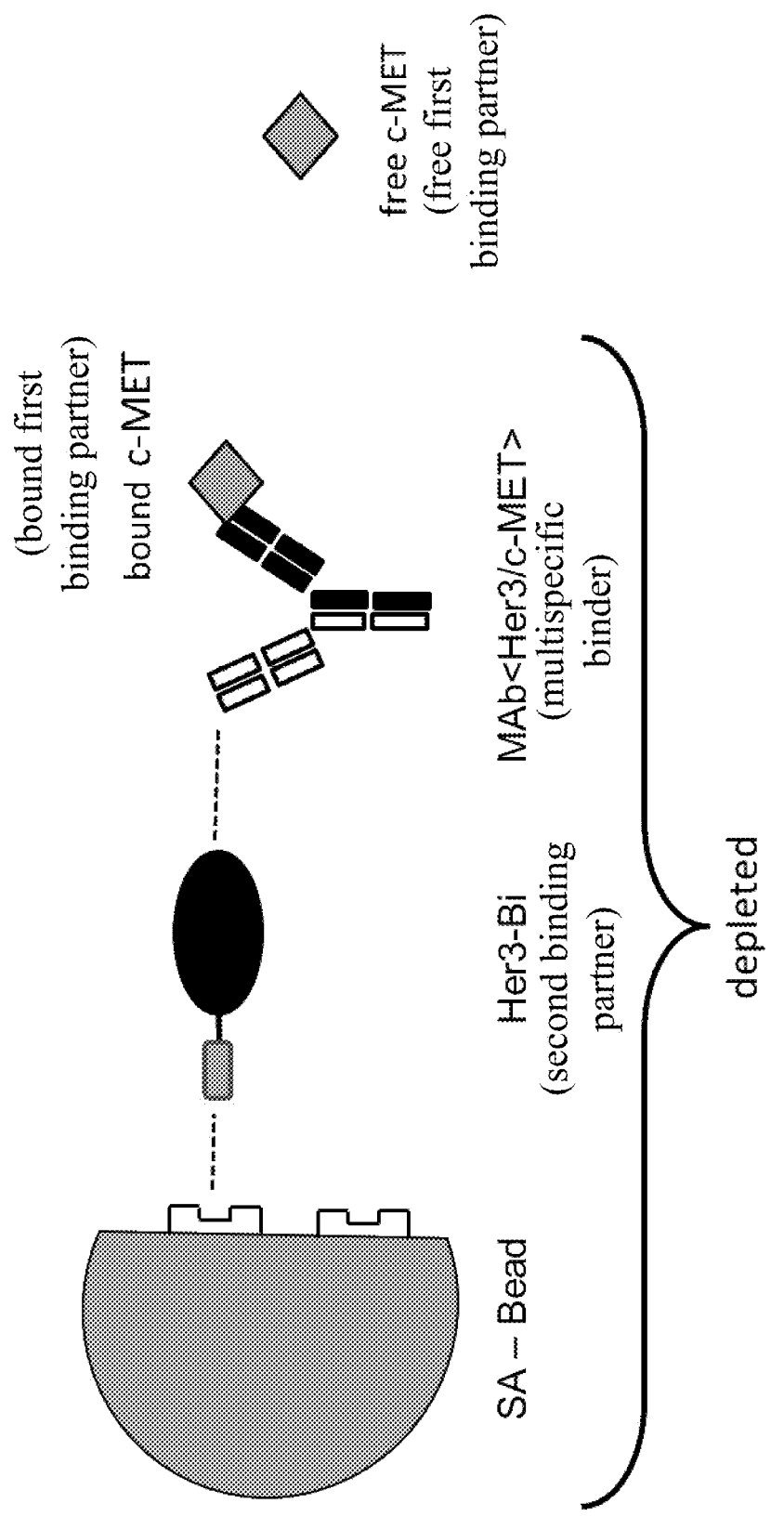
FIG. 2 Depletion of c-MET bound to a bispecific anti-c-MET/HER3 antibody by use of HER3; biotinylated HER3 immobilized on streptavidin-coated magnet-beads; after incubation of these magnet beads with a sample, e.g. serum sample, bispecific anti-c-MET/HER3 antibody is bound and depleted by immobilized HER3; c-MET bound to the bispecific antibody is co-depleted; free c-MET (not-bound to the bispecific antibody) remains in the supernatant of the sample.
Figure 3:
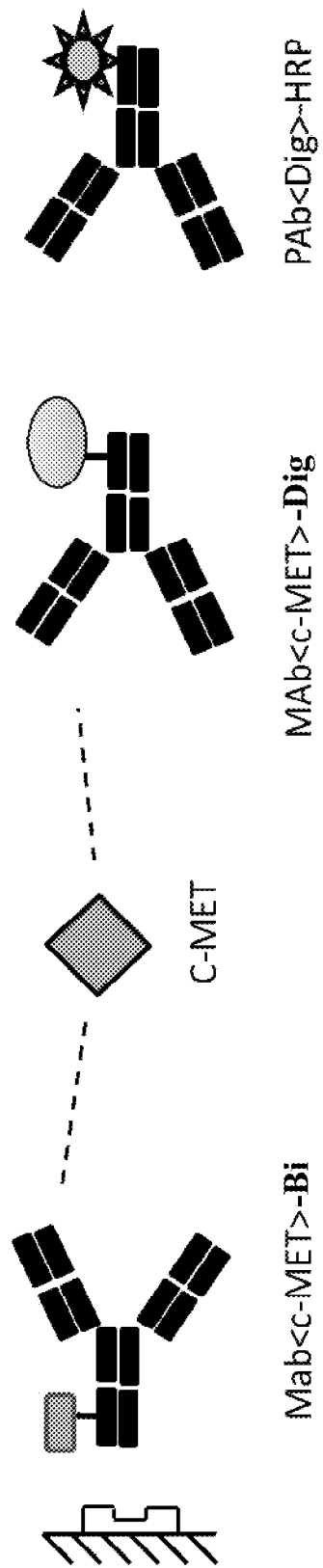
FIG. 3 Sandwich ELISA for detection of c-MET: biotinylated anti c-MET antibody is bound to a streptavidin coated microtiter plate; immobilized anti-c-MET antibody specifically binds free c-MET and a second, DIG-labeled anti-c-MET antibody allows detection of bound c-MET; the assay is used to detect "free" c-MET in the supernatant of a sample after depletion.

A biotinylated monoclonal antibody against c-MET was coated to a streptavidin microtiter plate in the first step. The supernatant sample from the depletion step (see Example 1) was diluted 10-fold and added to the wells of the anti-c-MET antibody coated microplate. Free c-MET contained in the sample was bound by the anti-c-MET antibody coated to wells of the microplate. After 1 hour incubation time at room temperature, the sample was removed by 3-times washing of the plate. Afterwards, a monoclonal DIG-labeled anti-c-MET antibody with a different specificity, i.e. epitope, than the coating antibody was added to the wells and incubated for another hour at room temperature. After another washing step, a polyclonal HRP labeled anti-DIG antibody was added to the plate and incubated for another hour. ABTS substrate solution was used to trigger a color reaction (see FIG. 3).

EXAMPLE 3

Depletion of Drug Bound c-MET in Human Serum and Buffer

Figure 4A:
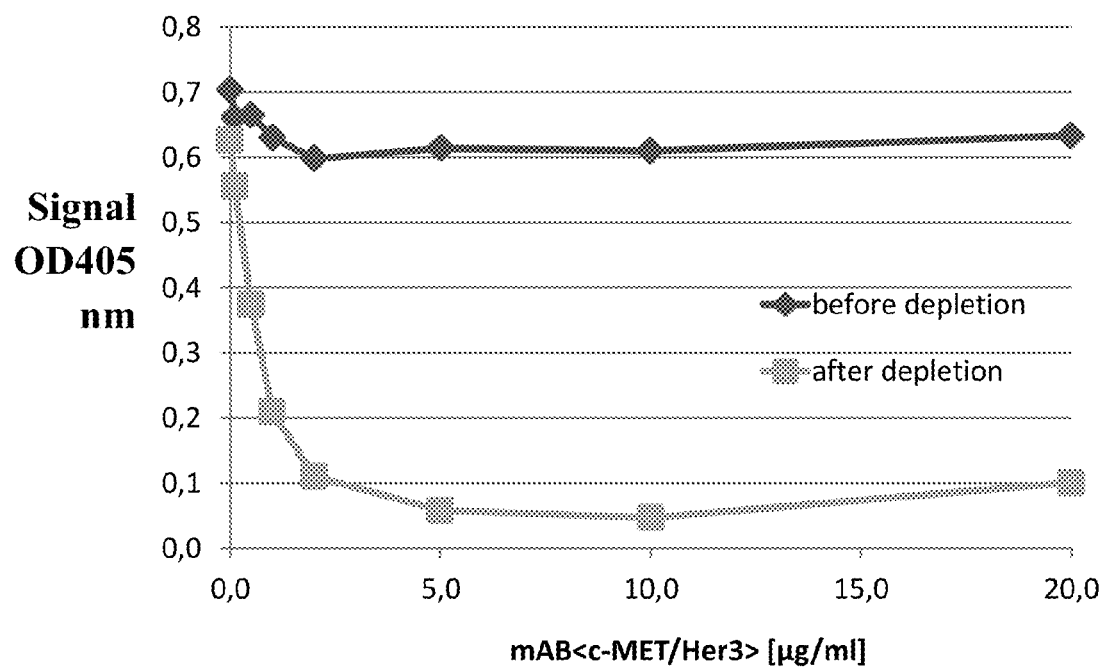
FIG. 4(A) Assay signal levels of c-MET before and after immuno depletion in buffer: samples with 100 ng/ml c-MET and increasing amount of bispecific anti-c-MET/HER3 antibody were prepared; complexes of bsmAb and bound c-MET were depleted with biotinylated HER3, bound to magnetic beads; the diagram shows c-MET concentrations before and after depletion determined by an ELISA.
Figure 4B:
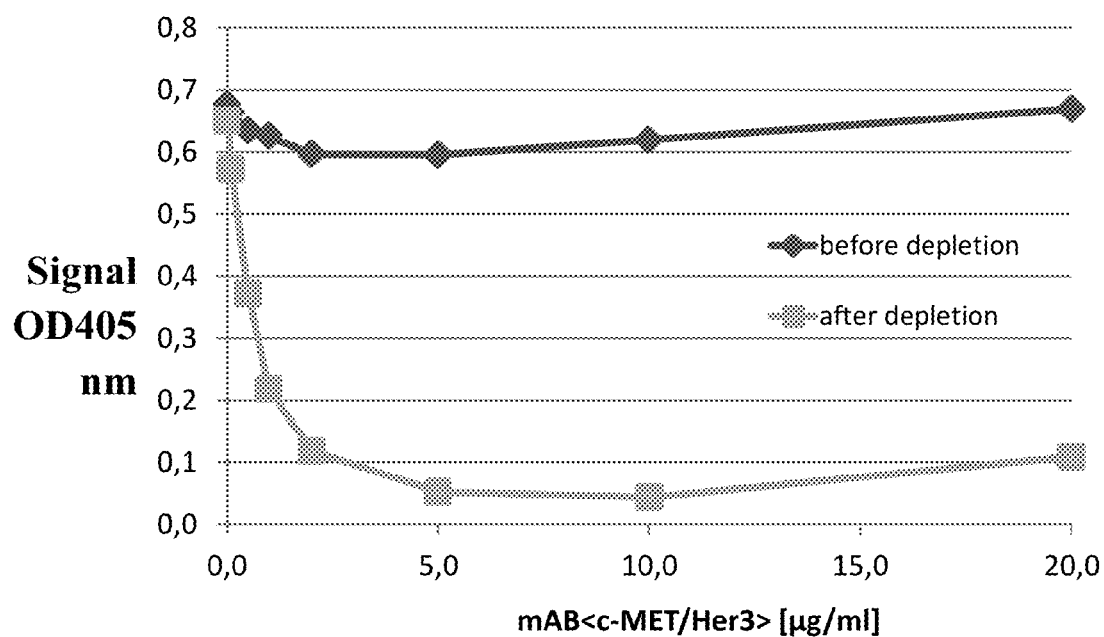
FIG. 4(B) Assay signal levels of c-MET before and after immuno depletion in serum: samples with 100 ng/ml c-MET and increasing amount of bispecific anti-c-MET/HER3 antibody were prepared; complexes of bsmAb and bound c-MET were depleted with biotinylated HER3, bound to magnetic beads; the diagram shows c-MET concentrations before and after depletion determined by an ELISA.

According to Example 1 bispecific anti-c-MET/HER3 antibody was diluted to a concentration of 20/10/5/1/0.5/0.1 and 0 μg/ml, respectively, and incubated with a constant concentration of 100 ng/ml c-MET. Dilutions were generated in two different matrices:

PBS/BSA buffer
Human Pool Serum (Trina, NHS Base matrix)
Samples were incubated at room temperature for 1 hour. Afterwards, samples were depleted as described in Example 1.
HER3-BI was used to capture complexes of c-MET with bispecific anti-c-MET/HER3 antibody.
After depletion Supernatant was measured in c-MET ELISA as described in Example 2.
As shown in FIG. 4a, c-MET, bound to the bispecific anti-c-MET/HER3 antibody is removed by immunodepletion. In presence of 5 μg/ml of bispecific antibody or higher, the c-MET signals after depletion are close to assay background signals.
Similar behavior was observed in serum samples as shown in FIG. 4b.

EXAMPLE 4

Figure 5A:
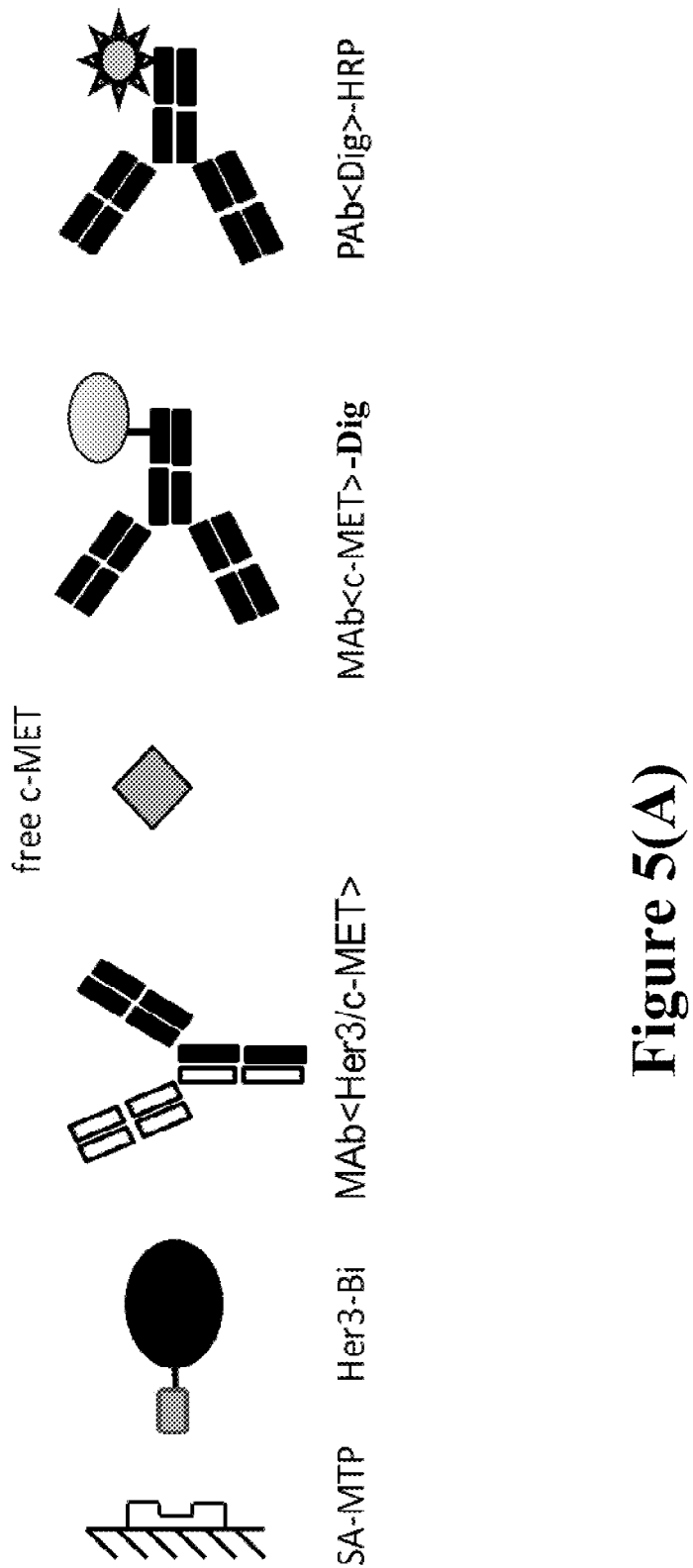
FIG. 5(A) ELISA to detect the antigen of a bispecific antibody by help of the other antigen: biotinylated HER3 is bound to a streptavidin coated microtiter plate and used to immobilize bispecific anti-c-MET/HER3 antibody; c-MET is bound to immobilized bispecific anti-c-MET/HER3 antibody; a second anti c-MET antibody (DIG-labeled) together with a polyclonal, HRP labeled anti-DIG antibody allows detection of bound c-MET.

ELISA to Detect the Antigen of a Bispecific Antibody by Help of the Other Antigen
a) Detection of the Amount of (Total) c-MET in a Sample
Biotinylated HER3 was bound to a streptavidin microtiter plate in the first step. In parallel, the bispecific anti-c-MET/HER3 antibody was pre-incubated for 1 hour with a sample/standard. c-MET in the sample was bound to bifunctional anti-c-MET/HER3 antibody during pre-incubation. After washing of the streptavidin coated plate the pre-incubated mixture of c-MET and anti-c-MET/HER3 antibody was added to the plate and incubated for 1 hour at room temperature. After another washing step to remove unbound components from the sample, a digoxigenin labeled anti-c-MET antibody (binding to a different epitope to c-MET as the bifunctional anti-c-MET/HER3 antibody) was added and incubated for one hour. After another washing step, a polyclonal horseradish peroxidase (HRP) labeled anti-DIG antibody was added to the plate and incubated for one hour. ABTS substrate solution was used to trigger a color reaction (see FIG. 5a).

b) Detection of (Pre-Existing) Complexes of Bispecific Anti-c-MET/HER3 Antibody and c-MET in a Sample
Biotinylated HER3 was bound to a streptavidin microtiter plate in the first step. After washing of the plate samples and standards were added to the plate and incubated for one hour at room temperature. Complexes of bispecific anti-c-MET/HER3 antibody and c-MET were bound to immobilized HER3-BI. After another washing step, a digoxigenin labeled anti-c-MET antibody that specifically binds to a different epitope of c-MET as the bifunctional anti-c-MET/HER3 antibody was added and incubated for one hour. After another washing step, a polyclonal HRP labeled anti-DIG antibody was added to the plate and incubated for one hour. ABTS substrate solution was used to trigger a color reaction (see FIG. 5(A)).

EXAMPLE 5

Figure 5B:
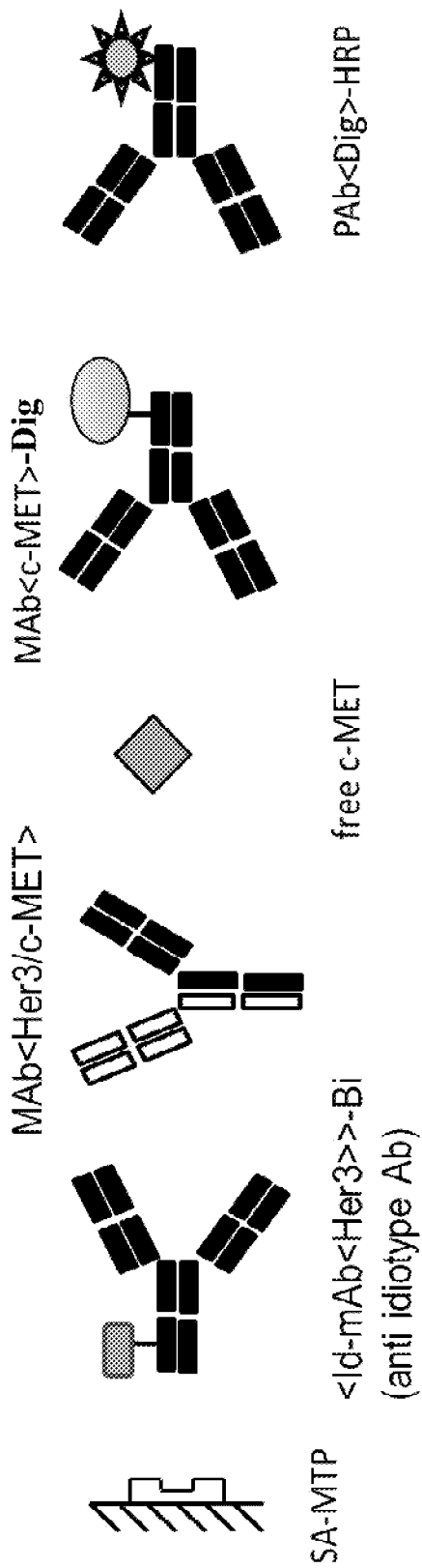
FIG. 5(B) ELISA to detect the antigen of a bispecific antibody by help of an anti-idiotypic antibody against the other binding specificity of this bispecific antibody: biotinylated anti-idiotypic antibody against the binding specificity, which specifically binds to HER3 (idmAb<HER3>-BI) is bound to a streptavidin coated microtiter plate and used to immobilize bispecific anti-c-MET/HER3 antibody; c-MET is bound to immobilized bispecific anti-c-MET/HER3 antibody; a second anti-c-MET antibody (DIG-labeled) together with a polyclonal, HRP labeled anti-DIG antibody allows detection of bound c-MET.
Figure 6:
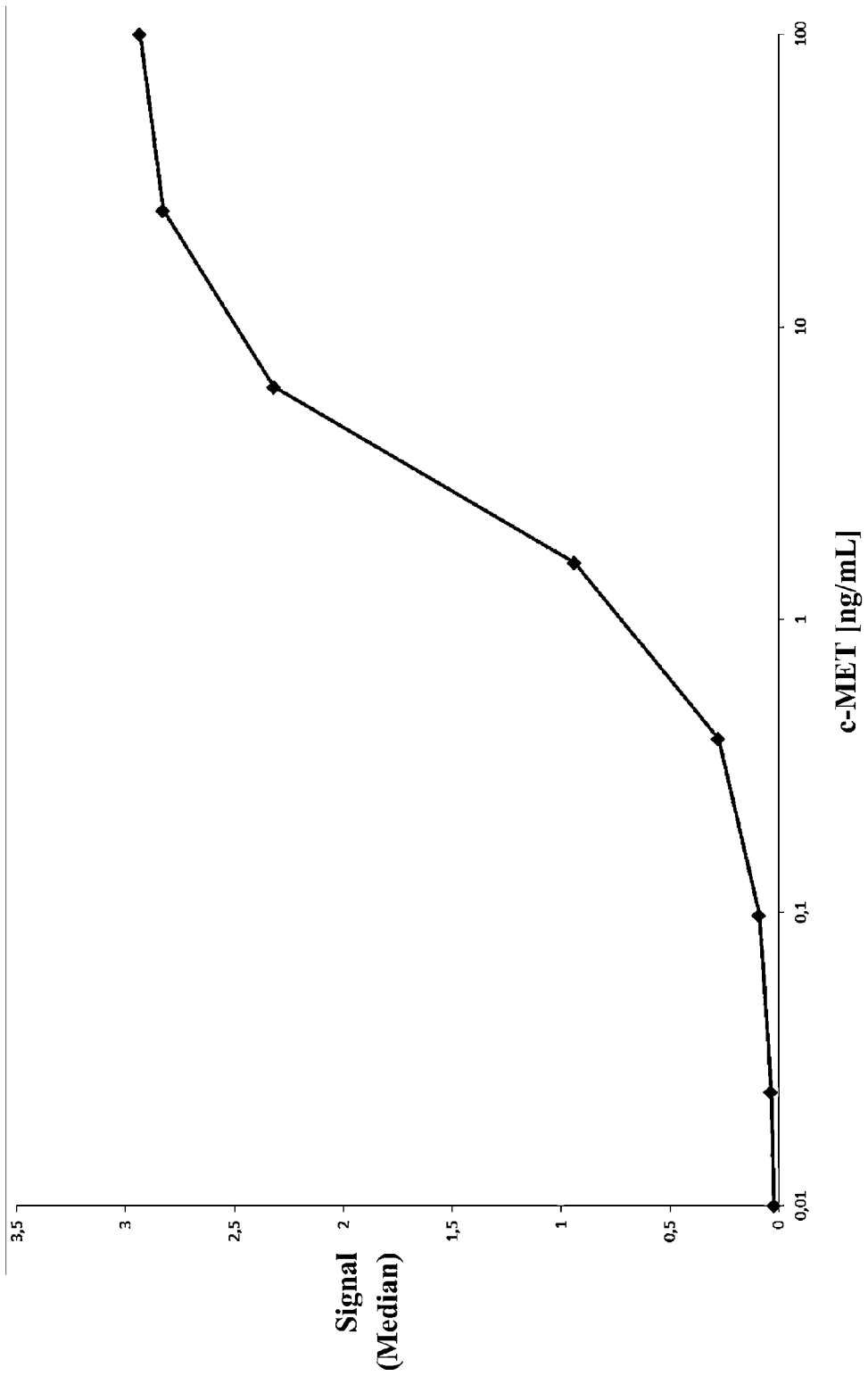
FIG. 6 Calibration curve of ELISA to detect the antigen of a bispecific antibody by help of the other antigen.

ELISA to Detect the First Antigen of a Bispecific Antibody by Help of an Anti-idiotypic Antibody Against the Second Binding Specificity of this Bispecific Antibody
a) Detection of the Amount of (Total) c-MET in a Sample
Biotinylated anti-idiotypic antibody against the binding specificity which specifically binds to HER3 (anti-idiotypic anti-HER3 antibody antibody-BI) is bound to a streptavidin coated microtiter plate in the first step. In parallel, the bispecific anti-c-MET/HER3 antibody is pre-incubated for one hour with a sample or standard. c-MET in the sample is specifically bound by the bispecific anti-c-MET/HER3 antibody in the pre-incubation step. After washing of the streptavidin coated plate, pre-incubated mixture of c-MET and bispecific anti-c-MET/HER3 antibody is added to the plate and incubated for one hour at room temperature. After another washing step to remove unbound components a digoxigenin labeled anti-c-MET antibody (that specifically binds to a different epitope of c-MET as the bispecific anti-c-MET/HER3 antibody is added and incubated for one hour. After another washing step, a polyclonal HRP labeled anti-DIG antibody is added to the plate and incubated for another hour. ABTS substrate solution is used to trigger a color reaction (see FIG. 5(B)).

b) Detection of (Pre-Existing) Complexes of Anti-c-MET/HER3 Antibody and c-MET in a Sample
Biotinylated anti-idiotypic antibody against the binding specificity which specifically binds to HER3 (anti-idiotypic anti-HER3 antibody antibody-BI) is bound to a streptavidin coated microtiter plate in the first step. After washing of the plate, samples and standards are added to the plate for one hour at room temperature. Complexes of anti-c-MET/HER3 antibody and c-MET is captured by immobilized anti-idiotypic antibody. After another washing step, a digoxigenin labeled anti-c-MET antibody with that specifically binds to a different epitope of c-MET as the bispecific anti-c-MET/HER3 antibody is added and incubated for one hour. After another washing step, a polyclonal HRP labeled anti-DIG antibody is added to the plate and incubated for one hour. ABTS substrate solution is used to trigger a color reaction (see FIG. 5(B)).

EXAMPLE 6

Figure 7:
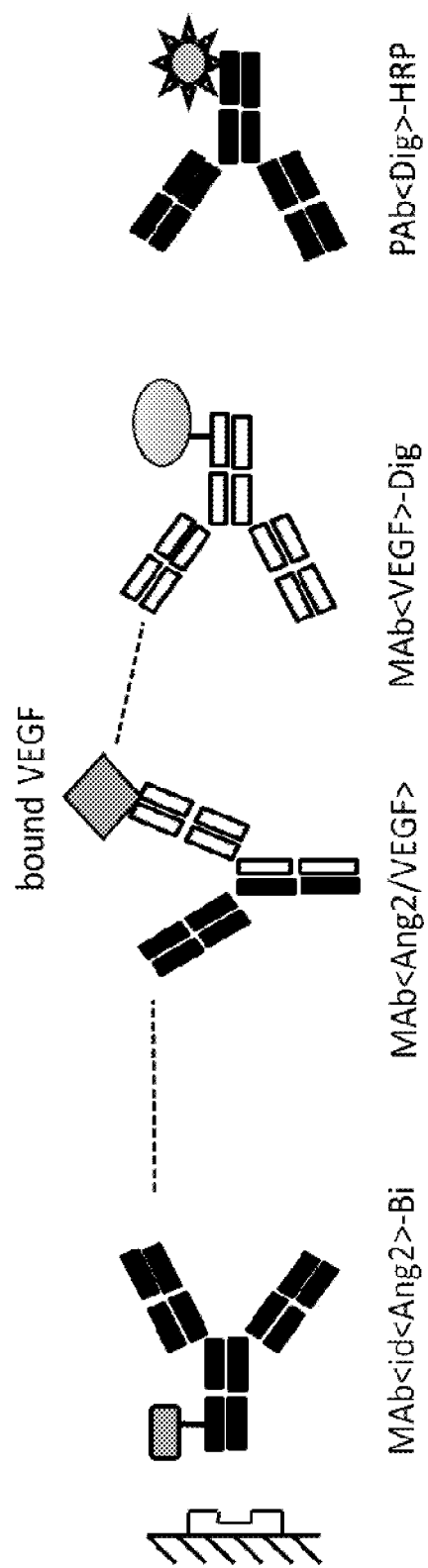
FIG. 7 Sandwich ELISA for detection of VEGF with an anti-ANG2/VEGF antibody (VEGF bound by a bispecific antibody): A biotinylated anti-idiotypic antibody against the ANG2 binding specificity of the bispecific antibody is bound to a streptavidin coated micro titer plate. Immobilized anti-idiotypic anti-ANG2 antibody forms a complex with the anti-ANG2/VEGF antibody. A second digoxigenin-labeled anti-VEGF antibody is used for the detection of bispecific antibody-bound VEGF.
Figure 8:
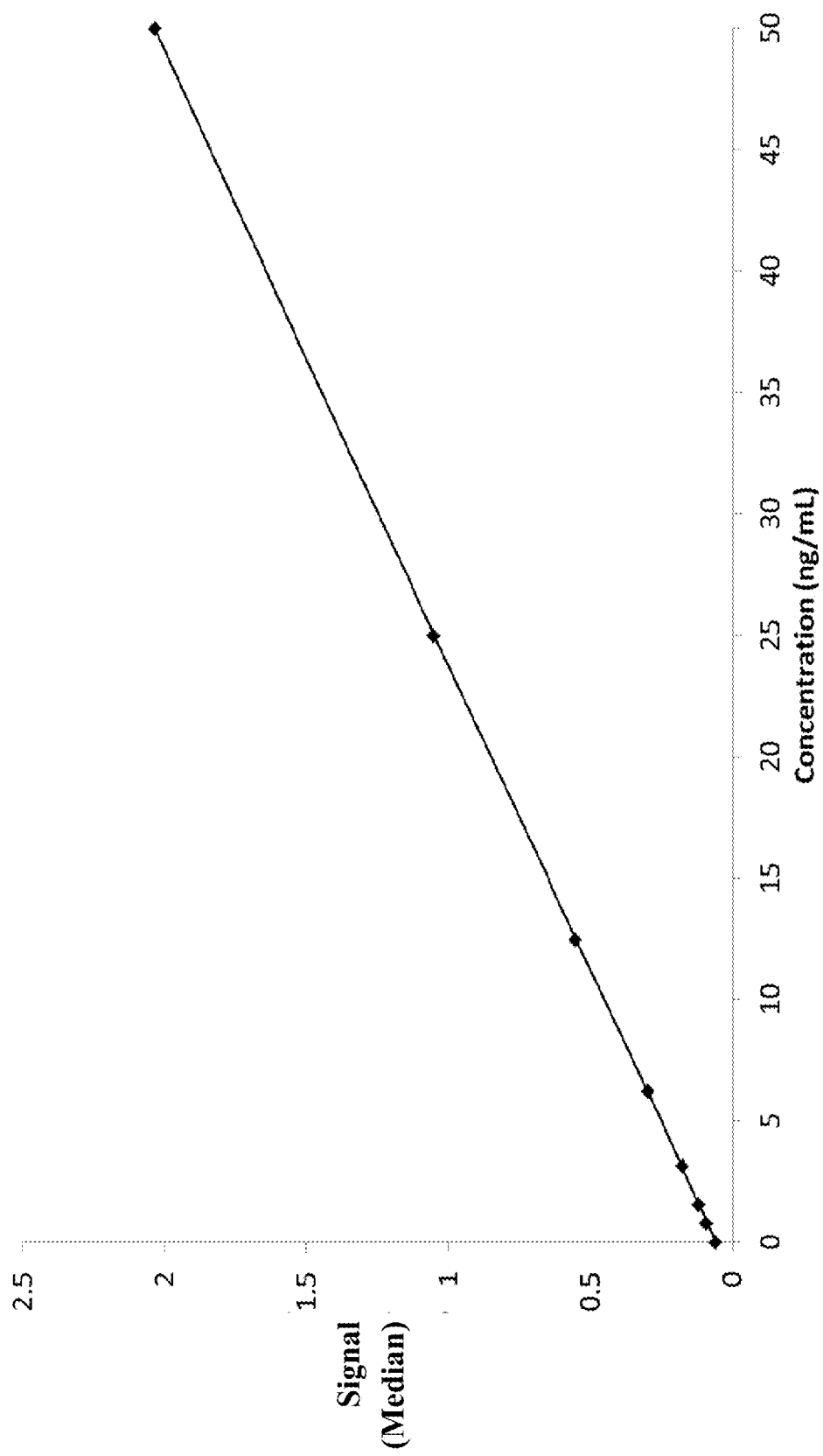
FIG. 8 Calibration curve of an ELISA for detection of complexes of VEGF with an anti-ANG2/VEGF antibody. A dilution series from 0 ng/ml to 50 ng/ml VEGF was added to serum containing 500 µg/ml anti-ANG2/VEGF antibody and incubated for 1 hour at room temperature. Samples were analyzed as described in Example 6.

ELISA for Detection of Complexes of VEGF with an Anti-ANG2/VEGF Bispecific Antibody A biotinylated monoclonal anti-idiotypic anti-ANG2 antibody antibody that specifically binds to the ANG2 binding specificity of an anti-ANG2/VEGF antibody was coated to a streptavidin coated micro titer plate (MTP). A sample with unknown amount of a complex of VEGF with the anti-ANG2/VEGF antibody was diluted 10-fold and added to the wells of the anti-idiotypic anti-ANG2 antibody antibody-coated MTP. The bispecific antibody specifically binding to ANG2 and VEGF was complexed by the immobilized anti-idiotypic antibody against the CDRs of the ANG2 binding specificity of the bispecific antibody. Complexes of bispecific antibody and VEGF were also bound. After one hour incubation time at room temperature the sample/supernatant was removed, followed by 3-times wash of the plate. Afterwards, a monoclonal digoxigenin-labeled anti-VEGF antibody (which binds to a different epitope on VEGF than the bispecific anti-ANG2/VEGF antibody to be detected) was added to the wells and incubated for one hour at room temperature. After a washing step, a polyclonal horseradish peroxidase (HRP) labeled anti-digoxigenin antibody (anti-DIG antibody) was added to the plate and incubated for one hour. After removal of supernatant and washing, ABTS substrate solution was added for the color reaction (see FIG. 7).

EXAMPLE 7

Figure 9:
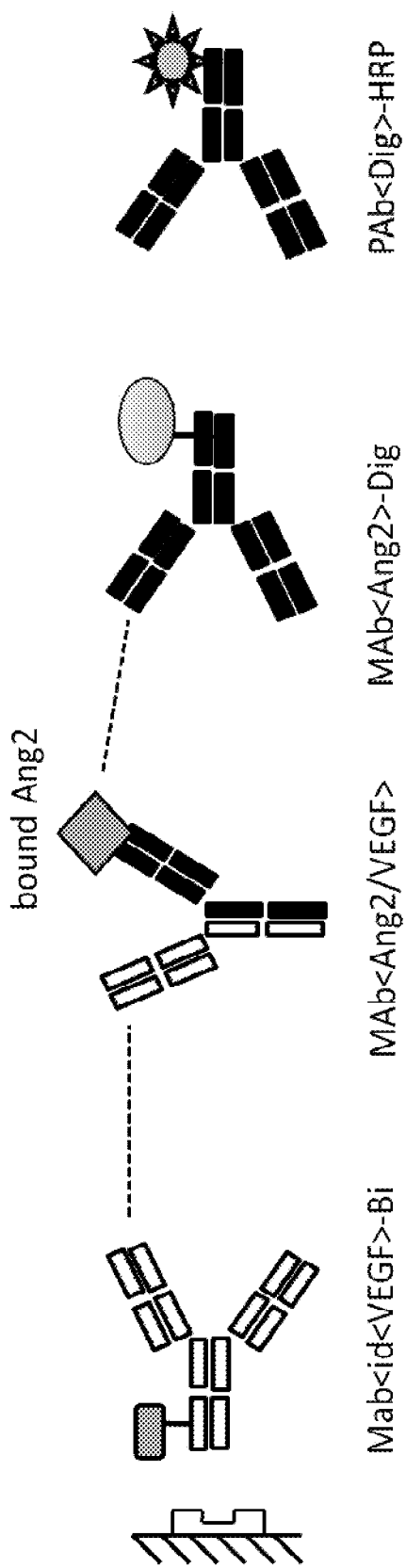
FIG. 9 Sandwich ELISA for detection of complexes of ANG2 with anti-ANG2/VEGF antibody (ANG2-bound by bispecific antibody): A biotinylated anti-idiotypic antibody against the VEGF binding specificity of the bispecific antibody is bound to a streptavidin coated micro titer plate. Immobilized anti-idiotypic anti-VEGF antibody antibody forms a complex with the anti-ANG2/VEGF antibody. A second digoxigenin-labeled anti-ANG2 antibody is used for the detection of bound ANG2.
Figure 10:
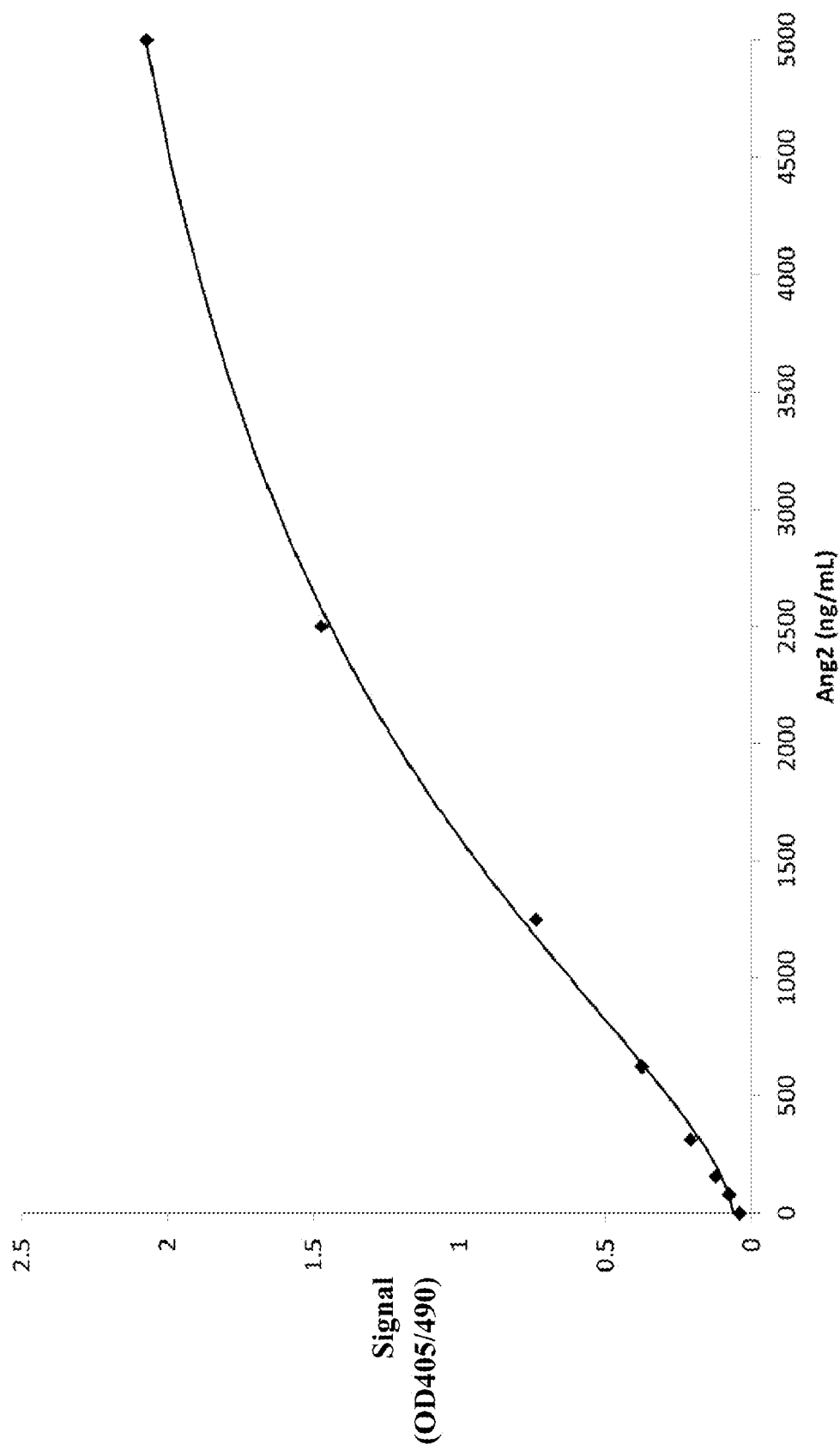
FIG. 10 Calibration curve of ELISA for detection of complexes of ANG2 with anti-ANG2/VEGF antibody. A dilution series from 0 ng/ml to 5000 ng/ml ANG2 was added to serum containing 5 µg/ml anti-ANG2/VEGF antibody and incubated for 1 hour at room temperature. Samples were analyzed as described in Example 7.

ELISA for Detection of Complexes of ANG2 with a Bispecific Anti-ANG2/VEGF Antibody A biotinylated monoclonal anti-idiotypic antibody that specifically binds to the VEGF binding specificity of an anti-ANG2/VEGF antibody was coated to a streptavidin coated micro titer plate (MTP). A sample with unknown amount of complexes of ANG2 with the anti-ANG2/VEGF antibody was diluted 10-fold and added to the wells of the anti-idiotypic anti-VEGF antibody antibody coated MTP. The bispecific antibody specifically binding to ANG2 and VEGF was complexed by the immobilized anti-idiotypic antibody against the CDRs of VEGF binding specificity of the bispecific anti-ANG2/VEGF antibody. Complexes of bispecific antibody and ANG2 were also bound. After one hour incubation at room temperature, the sample/supernatant was removed, followed by 3-times washing of the plate. Afterwards, a monoclonal digoxigenin-labeled anti-ANG2 antibody (that specifically binds to a different epitope than the ANG2 binding specificity of the bispecific anti-ANG2/VEGF antibody) was added to the wells and incubated for one hour at room temperature. After a washing step, a polyclonal HRP labeled anti-digoxigenin antibody was added to the plate and incubated for one hour. After removal of supernatant and washing, ABTS substrate solution was added for the color reaction (see FIG. 9).

EXAMPLE 8

Figure 11:
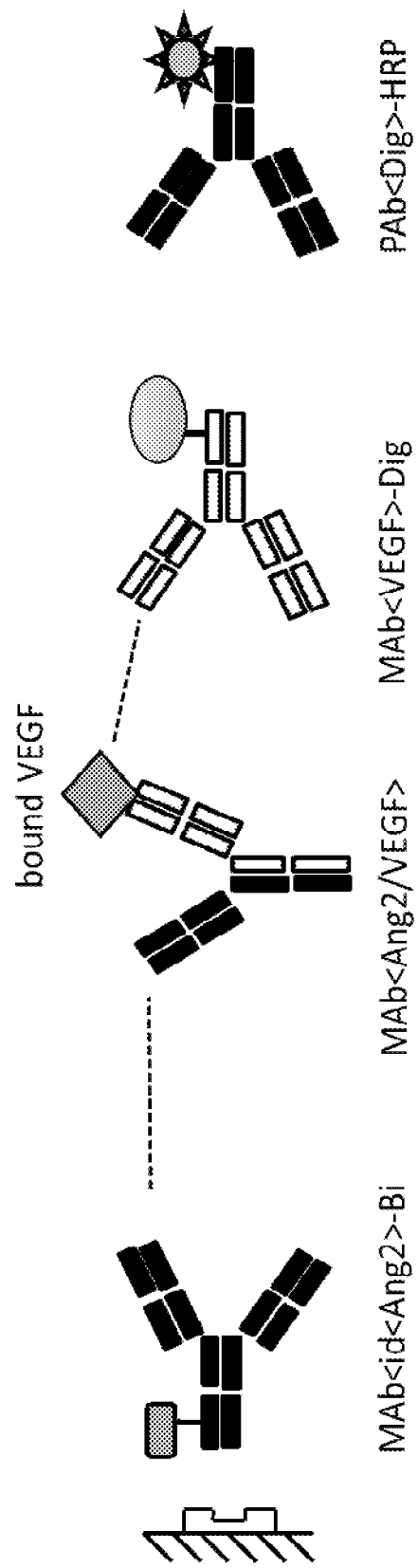
FIG. 11 Sandwich ELISA for detection of complexes of VEGF with anti-ANG2/VEGF antibody (VEGF-bound by bispecific antibody): A biotinylated anti-VEGF antibody is bound to a streptavidin coated micro titer plate. Immobilized anti-VEGF antibody forms a complex with the anti-ANG2/VEGF antibody-VEGF complex. A digoxigenin-labeled anti-idiotypic anti-ANG2 antibody antibody is used for the detection of antibody-bound complex.
Figure 12:
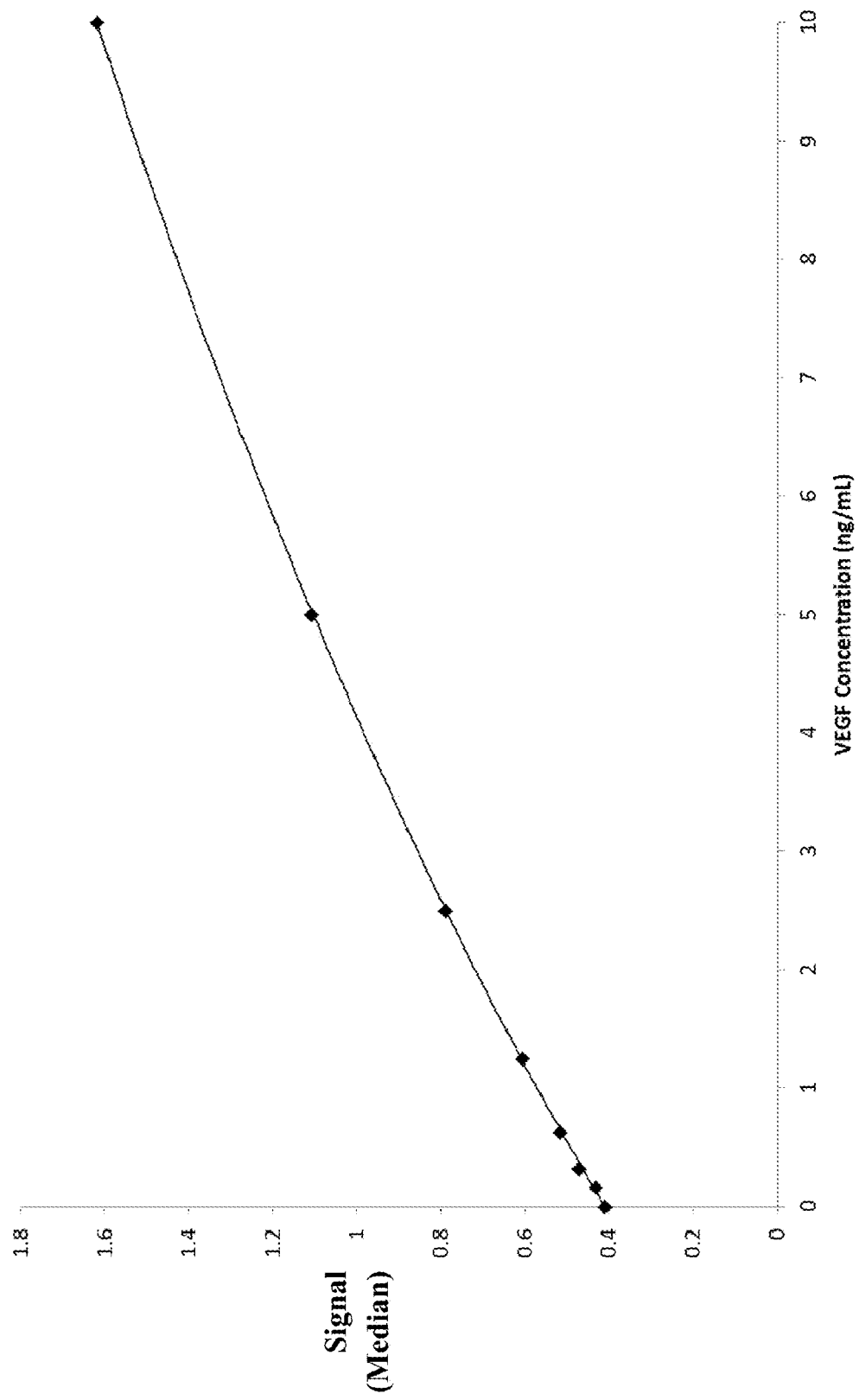
FIG. 12 Calibration curve of ELISA for detection of complexes of VEGF with anti-ANG2/VEGF antibody. A dilution series from 0 ng/ml to 10 ng/ml VEGF was added to serum containing anti-ANG2/VEGF antibody and incubated for 1 hour at room temperature.

ELISA for Detection of Complexes of VEGF with a Bispecific Anti-ANG2/VEGF Antibody A biotinylated monoclonal antibody against VEGF was coated to a streptavidin coated micro titer plate (MTP). After washing, a sample with unknown amount of complexes of VEGF with an anti-ANG2/VEGF antibody was diluted 10-fold and added to the wells of the anti-VEGF antibody coated MTP. The immobilized antibody against VEGF binds VEGF at a different binding site compared to the bispecific anti ANG2/VEGF antibody. Complexes of VEGF with an anti-ANG2/VEGF antibody bind to the immobilized anti VEGF antibody. After one hour incubation at room temperature, the sample/supernatant was removed, followed by 3-times washing of the plate. Afterwards, a digoxigenin labeled monoclonal anti-idiotypic antibody that specifically binds to the ANG2 binding specificity of the anti-ANG2/VEGF antibody was added to the wells and incubated for one hour at room temperature. After a washing step, a polyclonal HRP labeled anti-digoxigenin antibody was added to the plate and incubated for one hour. After removal of supernatant and washing, ABTS substrate solution was added for the color reaction (see FIG. 11). A corresponding calibration curve is shown in FIG. 12.

EXAMPLE 9

Figure 13:
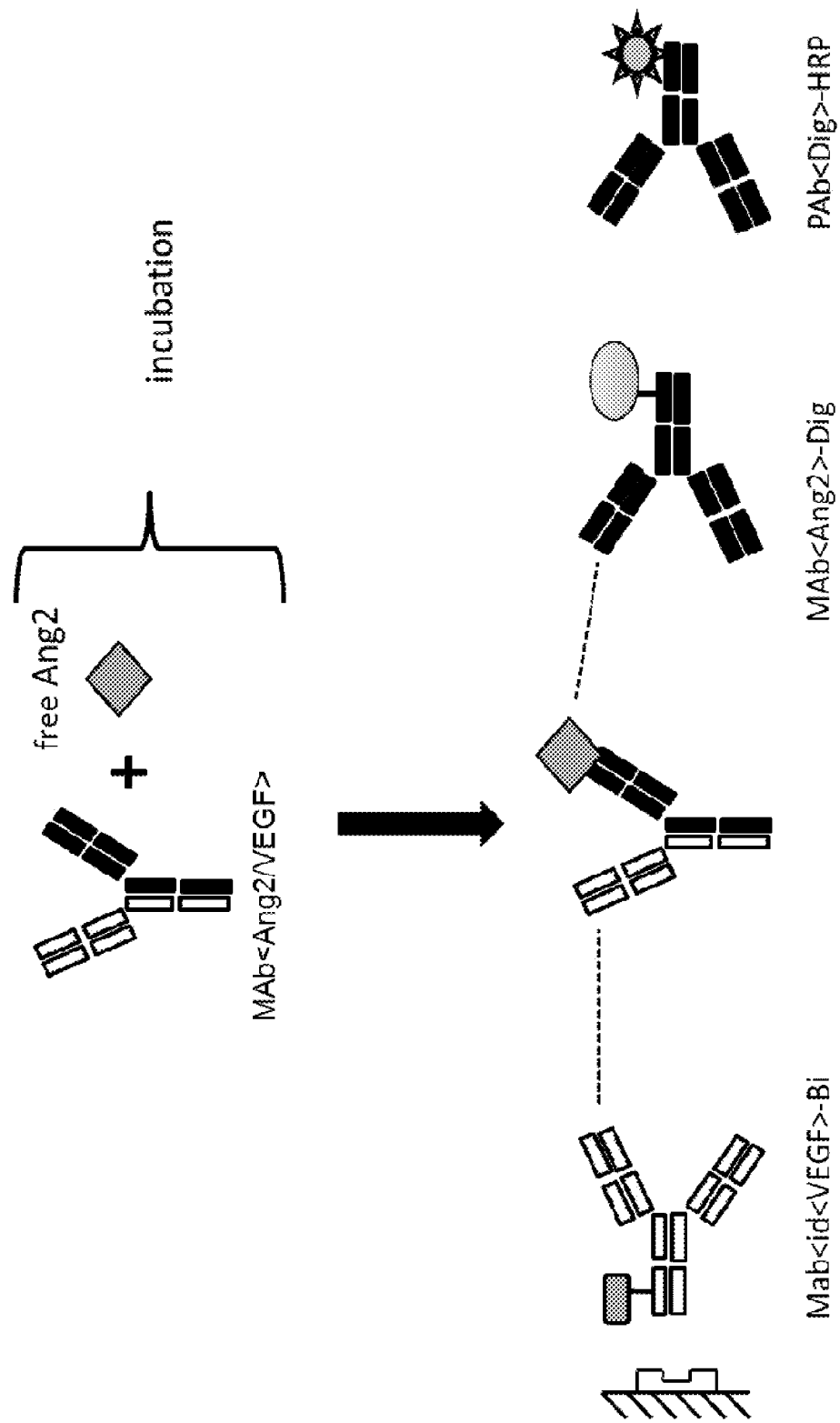
FIG. 13 Sandwich ELISA for detection of complexes of ANG2 with anti-ANG2/VEGF antibody (ANG2-bound by bispecific antibody): Free ANG2 is converted to antibody-bound ANG2 by the incubation of the sample with a bispecific anti-ANG2/VEGF antibody. A biotinylated anti-idiotypic antibody against the VEGF binding specificity of the bispecific antibody is bound to a streptavidin coated micro titer plate. Immobilized anti-idiotypic anti-VEGF antibody antibody forms a complex with the ANG2-anti-ANG2/VEGF antibody complex. A second digoxigenin-labeled anti-ANG2 antibody that specifically binds to a different epitope on ANG2 than the anti-ANG2/VEGF antibody is used for the detection of total ANG2.

ELISA for Detection of Total ANG2 by Conversion of Free ANG2 to Antibody-Bound ANG2 and Incubation with a Bispecific Anti-ANG2/VEGF Antibody A biotinylated monoclonal anti-idiotypic antibody that specifically binds to the VEGF binding specificity of an anti-ANG2/VEGF antibody was bound to a streptavidin coated micro titer plate (MTP). A first aliquot of a sample with unknown amount of ANG2 was incubated for one hour with 1.5 µg/mL bispecific anti-ANG2/VEGF antibody in order to convert free ANG2 to anti-ANG2/VEGF antibody-bound ANG2. The second (i.e. the not incubated) aliquot of the sample and the antibody incubated aliquot of the sample were diluted 10-fold and added to the wells of the MTP coated with the anti-idiotypic antibody that specifically binds to the VEGF binding specificity of the bispecific antibody. The bispecific antibody was bound by the immobilized anti-idiotypic antibody. Likewise complexed ANG2 was bound via the bispecific antibody. After an incubation time of one hour at room temperature, the supernatant (=sample) was removed, followed by 3-times washing of the plate. Afterwards, a monoclonal digoxigenin-labeled anti-ANG2 antibody (that specifically binds to a different epitope than the ANG2 binding specificity of the bispecific anti-ANG2/VEGF antibody) was added to the wells and incubated for one hour at room temperature. After a washing step, a polyclonal HRP labeled anti-digoxigenin antibody was added to the plate and incubated for one hour. After removal of supernatant and washing, ABTS substrate solution was added for the color reaction (see FIG. 13). From the difference between the result obtained for the first aliquot and the result obtained for the second aliquot the amount of free ANG2 was calculated. Thus, with this assay the amount of antibody-bound ANG2 and free ANG2 was determined.

The invention claimed is:

1. A method for determining the presence and/or the amount of an antigen of a bispecific antibody in a sample, wherein the antigen to be detected can be specifically bound by a first binding specificity of the bispecific antibody, and wherein the antigen is complexed to the bispecific antibody (antigen-bispecific antibody-complex), comprising
   incubating the sample comprising the antigen and the bispecific antibody with an anti-idiotypic antibody, which specifically binds to a second binding specificity of the bispecific antibody, which is different from the first binding specificity, wherein the anti-idiotypic antibody is bound to a solid phase, under conditions where an antigen-bispecific antibody-anti-idiotypic antibody complex can be formed; and incubating the antigen-bispecific antibody-anti-idiotypic antibody complex with an antibody that specifically binds to the antigen at an epitope different from the epitope bound by the bispecific antibody;

and determining the presence and/or the amount of the antigen of the bispecific antibody which is complexed to the bispecific antibody in a sample.

2. The method according to claim 1, further comprising the step of:

detecting the antigen-bispecific antibody-anti-idiotypic antibody complex and thereby determining the presence and/or the amount of the antigen of the bispecific antibody.

3. The method according to claim 1 comprising the following steps:

providing the sample comprising the antigen and the bispecific antibody, wherein at least 90% of the antigen are complexed by the bispecific antibody in the antigen-bispecific antibody complex, wherein the antigen to be detected can be specifically bound by the first binding specificity of the bispecific antibody;

incubating the sample comprising the antigen and the bispecific antibody with the anti-diotypic antibody, which specifically binds to the second binding specificity of the bispecific antibody, which is different from the first binding specificity, wherein the anti-idiotypic antibody is bound to the solid phase; and incubating the antigen-bispecific antibody complex with the antibody that specifically binds to the antigen at an epitope different from the epitope bound by the bispecific antibody, and thereby determining the presence and/or the amount of the antigen of the bispecific antibody in the sample.

4. The method according to claim 1, comprising the following steps:

incubating the sample comprising the antigen and the bispecific antibody with an amount of the bispecific antibody to provide a sample wherein at least 90% of the antigen is complexed by the bispecific antibody in the antigen-bispecific antibody complex, wherein the antigen to be detected can be specifically bound by the first binding specificity of the bispecific antibody;

incubating the sample comprising the antigen-bispecific antibody complex with the anti-idiotypic antibody, which specifically binds to the second binding specificity of the bispecific antibody, which is different from the first binding specificity, wherein the anti-idiotypic antibody is bound to the solid phase, and wherein the antigen-bispecific antibody-anti-idiotypic antibody complex can be formed; and incubating the antigen-bispecific antibody-anti-idiotypic antibody complex with the antibody that specifically binds to the antigen at an epitope different from the epitope bound by the bispecific antibody, and thereby determining the presence and/or the amount of the antigen of the bispecific antibody in the sample.

5. The method according to claim 4, wherein the amount of the bispecific antibody is between 1 µg/ml and 10 µg/ml sample.

6. The method according to claim 4, wherein at least 95% of the antigen is complexed by the bispecific antibody.

7. The method according to claim 6, wherein at least 98% of the antigen is complexed by the bispecific antibody.

8. A method for determining the amount of an antigen of a bispecific antibody that is complexed to the bispecific antibody in a sample comprising:

incubating a sample comprising the antigen and the bispecific antibody with an anti-idiotypic antibody, which specifically binds to a binding specificity of the bispecific antibody, which is different from the binding specificity by which the antigen is bound, wherein an antigen-bispecific antibody-anti-idiotypic antibody complex can be formed, wherein the anti-idiotypic antibody is bound to a solid phase; and incubating the antigen-bispecific antibody-anti-idiotypic antibody complex with an antibody that specifically binds to the antigen at an epitope that is different from the epitope bound by the bispecific antibody, and thereby determining the amount of an antigen of a bispecific antibody complexed to the bispecific antibody in a sample.

* * * * *